(12) United States Patent
El-Tanani et al.

(10) Patent No.: US 11,999,770 B2
(45) Date of Patent: Jun. 4, 2024

(54) PEPTIDES AND NANOPARTICLE FORMULATIONS THEREOF

(71) Applicant: University of Bradford, Bradford (GB)

(72) Inventors: Mohamed El-Tanani, Bradford (GB); Paul McCarron, Londonderry (IE); Ahmed Faheem, Sunderland (GB)

(73) Assignee: UNIVERSITY OF BRADFORD, Bradford (GB)

( * ) Notice: Subject to any disclaimer, the term of this patent is extended or adjusted under 35 U.S.C. 154(b) by 270 days.

(21) Appl. No.: 17/134,977

(22) Filed: Dec. 28, 2020

(65) Prior Publication Data
US 2021/0188929 A1 Jun. 24, 2021

Related U.S. Application Data

(62) Division of application No. 16/096,947, filed as application No. PCT/GB2017/051222 on May 2, 2017, now abandoned.

(30) Foreign Application Priority Data

Apr. 29, 2016 (GB) ..................................... 1607593

(51) Int. Cl.
| | |
|---|---|
| *C07K 14/47* | (2006.01) |
| *A61K 9/51* | (2006.01) |
| *A61P 35/00* | (2006.01) |
| *C07K 7/06* | (2006.01) |
| *C07K 7/08* | (2006.01) |
| *A61K 38/00* | (2006.01) |

(52) U.S. Cl.
CPC ............ *C07K 14/4703* (2013.01); *A61K 9/51* (2013.01); *A61K 9/5153* (2013.01); *A61P 35/00* (2018.01); *C07K 7/06* (2013.01); *C07K 7/08* (2013.01); *C07K 14/4722* (2013.01); *A61K 9/5146* (2013.01); *A61K 38/00* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 6,670,464 | B1 | 12/2003 | Shimkets et al. |
| 2003/0198990 | A1 | 10/2003 | Chang |
| 2005/0170457 | A1* | 8/2005 | Pool .......................... A61P 7/06 435/69.1 |
| 2008/0146511 | A1 | 6/2008 | Pessolani et al. |
| 2009/0062512 | A1 | 3/2009 | Hildebrand et al. |
| 2014/0357512 | A1 | 12/2014 | Yang et al. |
| 2015/0015335 | A1 | 1/2015 | Chen et al. |
| 2015/0153356 | A1 | 6/2015 | Meng et al. |

FOREIGN PATENT DOCUMENTS

| | | |
|---|---|---|
| CN | 101065138 A | 10/2007 |
| JP | 2004121132 A | 4/2004 |
| WO | 9958670 A1 | 11/1999 |
| WO | 0124810 A1 | 4/2001 |
| WO | 03092736 | 11/2003 |
| WO | 2006014744 A2 | 2/2006 |
| WO | 2011119484 A1 | 9/2011 |
| WO | 2013040142 A2 | 3/2013 |
| WO | 2013041925 A1 | 3/2013 |
| WO | 2013059907 A1 | 5/2013 |
| WO | 2013096862 A2 | 6/2013 |
| WO | 2013106913 A1 | 7/2013 |
| WO | WO2013106913 * | 7/2013 |
| WO | 2013143504 A1 | 10/2013 |
| WO | 2013151663 A1 | 10/2013 |

OTHER PUBLICATIONS

"GTP-binding nuclear protein Ran (GTPase Ran)(Ras-like protein TC4), P62826", DrivasGT. et at, UNIPROT, pp. 1-4.
"DATABASE UniProt [Online]. Aug. 16, 2004. XP002771204, retrieved from EBI accession No. UNIPROT:P62826. Database accession No. P62826, 12 pages.".
"Great Britain Search Report corresponding to Patent Application No. GB1607593.9, dated Feb. 15, 2017, 5 pages".
"International Search Report and Written Opinion, PCT/GB2017/051222, mailed Jul. 5, 2017, 20 pages.".
Haggag Ya , et al., "Nano-encapsulation of a novel anti-Ran-GTPase peptide for blockade of regulator of chromosome condensation 1 (RCC1) function in MDA-MB-231 breast cancer cells. International Journal of Pharmaceutics. 2017; 521: 40-53.".
Kamaly N , et al., "Targeted polymeric therapeutic nanoparticles: design, development and clinical translation. Chem Soc Rev. 2012; 41: 2971-3010.".
Lee Sy , et al., "Effects of mastoparan B and its analogs on the phospholipase D activity in L1210 cells. FEBS Letters. 1998; 432(1-2): 50-54.".
Munz C , et al., "Peptide analysis, stability studies, and structural modeling explain contradictory peptide motifs and unique properties of the NOD mouse MHC class II molecule H2-Ag7. Eur J Immunology. 2002;32(8):2105-2116.".
Nishijima H , et al., "Caffeine mimics adenine and 2'-deoxyadenosine, both of which inhibit the guanine-nucleotide exchange activity of RCC1 and the kinase activity of ATR. Genes to Cells. 2003; 8(5): 423-435.".
Renault L , et al., "Structural basis for guanine nucleotide exchange on ran by the regulator of chromosome condensation (RCC1). Cell. Apr. 2001; 105(2): 245-255.".
Van Rossenberg SMW , et al., "Stable polyplexes based on arginine-containing oligopeptides for in vivo gene delivery. Gene Therapy. 2004; 11(1-2): 457-464.".

* cited by examiner

*Primary Examiner* — Maury A Audet
(74) *Attorney, Agent, or Firm* — Myers Bigel, P.A.

(57) ABSTRACT

The present invention relates to peptides, methods for production of the same, nanoparticle formulations of the same and the use of these new peptides and nanoparticle formulations as inhibitors of protein-protein interactions, in particular for application in the treatment of diseases associated with overexpression of the RAN gene.

16 Claims, 15 Drawing Sheets

Specification includes a Sequence Listing.

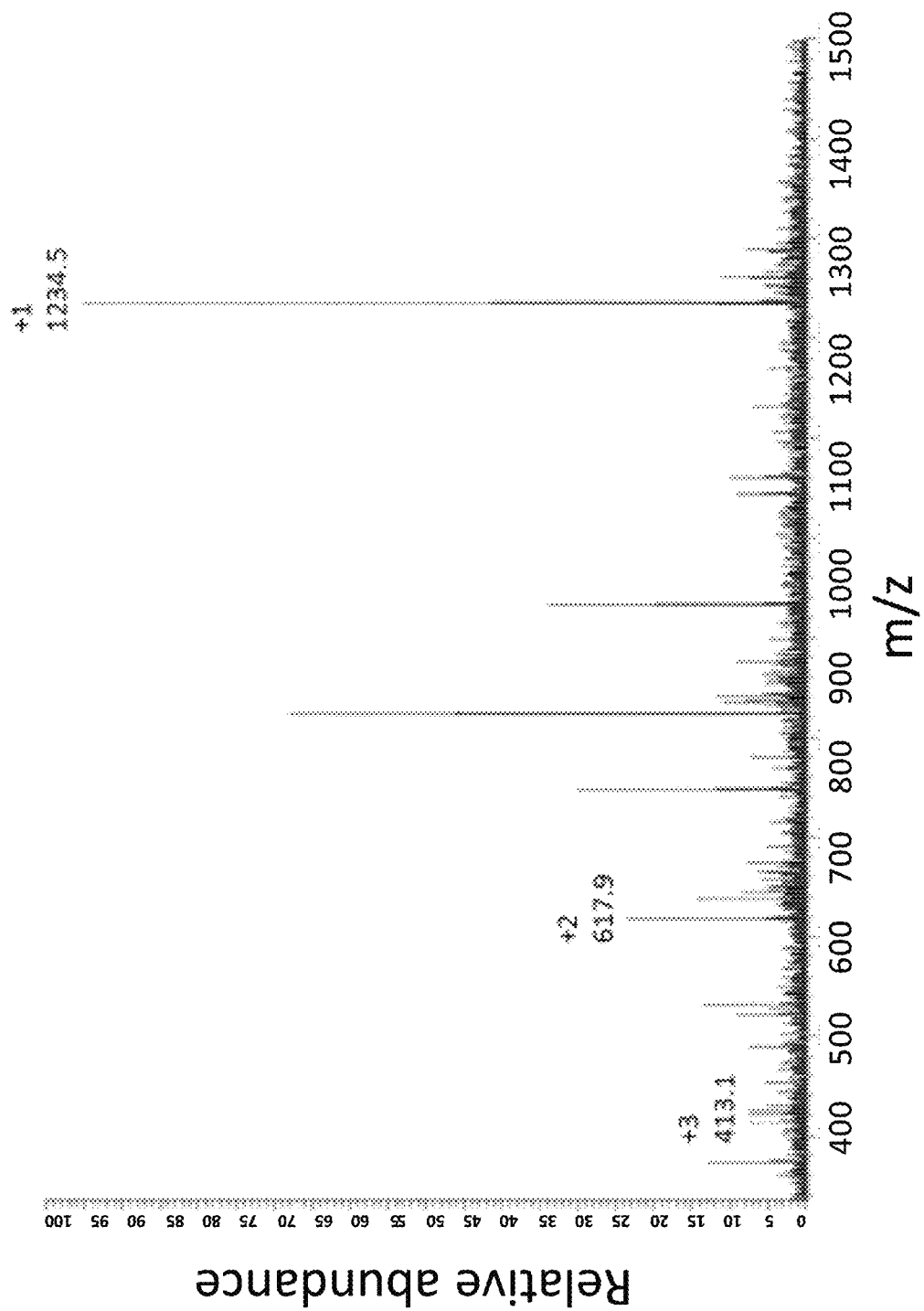
FIG. 5 con't

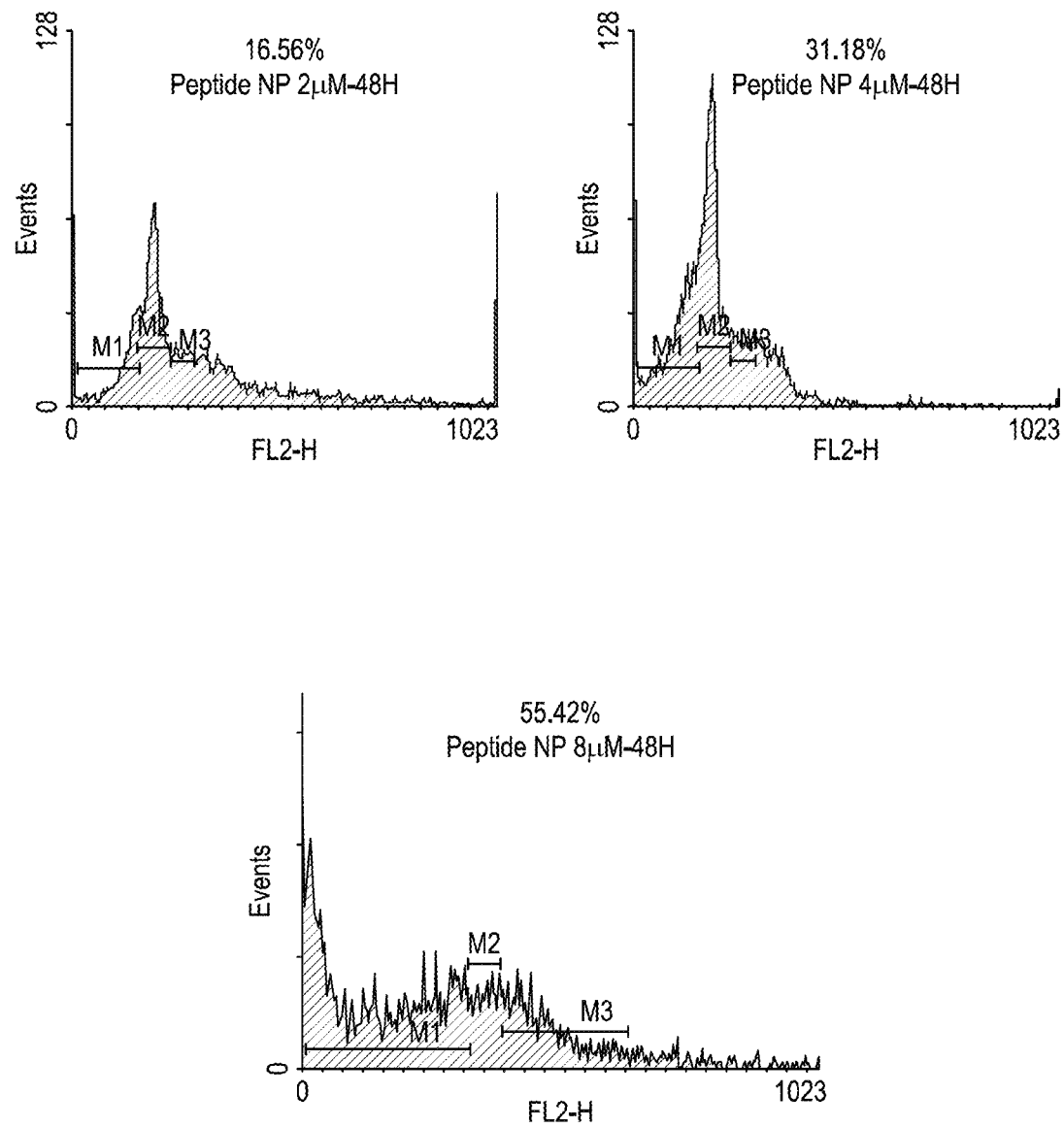
FIG. 9 con't

```
                         SEQUENCE LISTING

<160> NUMBER OF SEQ ID NOS: 22

<210> SEQ ID NO 1
<211> LENGTH: 216
<212> TYPE: PRT
<213> ORGANISM: Homo sapiens

<400> SEQUENCE: 1

Met Ala Ala Gln Gly Glu Pro Gln Val Gln Phe Lys Leu Val Leu Val
1               5                   10                  15

Gly Asp Gly Gly Thr Gly Lys Thr Thr Phe Val Lys Arg His Leu Thr
            20                  25                  30

Gly Glu Phe Glu Lys Lys Tyr Val Ala Thr Leu Gly Val Glu Val His
        35                  40                  45

Pro Leu Val Phe His Thr Asn Arg Gly Pro Ile Lys Phe Asn Val Trp
    50                  55                  60

Asp Thr Ala Gly Gln Glu Lys Phe Gly Gly Leu Arg Asp Gly Tyr Tyr
65                  70                  75                  80

Ile Gln Ala Gln Cys Ala Ile Ile Met Phe Asp Val Thr Ser Arg Val
                85                  90                  95

Thr Tyr Lys Asn Val Pro Asn Trp His Arg Asp Leu Val Arg Val Cys
            100                 105                 110

Glu Asn Ile Pro Ile Val Leu Cys Gly Asn Lys Val Asp Ile Lys Asp
        115                 120                 125

Arg Lys Val Lys Ala Lys Ser Ile Val Phe His Arg Lys Lys Asn Leu
    130                 135                 140

Gln Tyr Tyr Asp Ile Ser Ala Lys Ser Asn Tyr Asn Phe Glu Lys Pro
145                 150                 155                 160

Phe Leu Trp Leu Ala Arg Lys Leu Ile Gly Asp Pro Asn Leu Glu Phe
                165                 170                 175

Val Ala Met Pro Ala Leu Ala Pro Pro Glu Val Val Met Asp Pro Ala
            180                 185                 190

Leu Ala Ala Gln Tyr Glu His Asp Leu Glu Val Ala Gln Thr Thr Ala
        195                 200                 205

Leu Pro Asp Glu Asp Asp Leu
    210                 215

<210> SEQ ID NO 2
<211> LENGTH: 19
<212> TYPE: PRT
<213> ORGANISM: Artificial
<220> FEATURE:
<223> OTHER INFORMATION: Residues 129-142 of Ran

<400> SEQUENCE: 2

Met Ala Ala Gln Gly Glu Pro Gln Val Gln Phe Lys Leu Val Leu Val
1               5                   10                  15

Gly Asp Gly

<210> SEQ ID NO 3
<211> LENGTH: 14
<212> TYPE: PRT
<213> ORGANISM: Artificial
<220> FEATURE:
<223> OTHER INFORMATION: Residues 129-142 of Ran
```

<400> SEQUENCE: 3

Arg Lys Val Lys Ala Lys Ser Ile Val Phe His Arg Lys Lys
1               5                   10

<210> SEQ ID NO 4
<211> LENGTH: 20
<212> TYPE: PRT
<213> ORGANISM: Artificial
<220> FEATURE:
<223> OTHER INFORMATION: C-terminal region of Ran (residues 191 to 210)

<400> SEQUENCE: 4

Pro Ala Leu Ala Ala Gln Tyr Glu His Asp Leu Glu Val Ala Gln Thr
1               5                   10                  15

Thr Ala Leu Pro
            20

<210> SEQ ID NO 5
<211> LENGTH: 11
<212> TYPE: PRT
<213> ORGANISM: Artificial
<220> FEATURE:
<223> OTHER INFORMATION: synthetic

<400> SEQUENCE: 5

Cys Ala Gln Gly Glu Pro Gln Val Gln Phe Lys
1               5                   10

<210> SEQ ID NO 6
<211> LENGTH: 13
<212> TYPE: PRT
<213> ORGANISM: Artificial
<220> FEATURE:
<223> OTHER INFORMATION: synthetic

<400> SEQUENCE: 6

Cys Val Asp Ile Lys Asp Arg Lys Val Lys Ala Lys Ser
1               5                   10

<210> SEQ ID NO 7
<211> LENGTH: 15
<212> TYPE: PRT
<213> ORGANISM: Artificial
<220> FEATURE:
<223> OTHER INFORMATION: synthetic

<400> SEQUENCE: 7

Cys Gln Tyr Glu His Asp Leu Glu Val Ala Gln Thr Thr Ala Leu
1               5                   10                  15

<210> SEQ ID NO 8
<211> LENGTH: 11
<212> TYPE: PRT
<213> ORGANISM: Artificial
<220> FEATURE:
<223> OTHER INFORMATION: synthetic

<400> SEQUENCE: 8

Cys Glu Gln Gly Glu Pro Gln Val Gln Phe Lys
1               5                   10

<210> SEQ ID NO 9
<211> LENGTH: 11
<212> TYPE: PRT
<213> ORGANISM: Artificial

```
<220> FEATURE:
<223> OTHER INFORMATION: synthetic

<400> SEQUENCE: 9

Cys Ala Ser Gly Glu Pro Gln Val Gln Phe Lys
1               5                   10

<210> SEQ ID NO 10
<211> LENGTH: 11
<212> TYPE: PRT
<213> ORGANISM: Artificial
<220> FEATURE:
<223> OTHER INFORMATION: synthetic

<400> SEQUENCE: 10

Cys Ala Gln Met Glu Pro Gln Val Gln Phe Lys
1               5                   10

<210> SEQ ID NO 11
<211> LENGTH: 11
<212> TYPE: PRT
<213> ORGANISM: Artificial
<220> FEATURE:
<223> OTHER INFORMATION: synthetic

<400> SEQUENCE: 11

Cys Ala Gln Gly Phe Pro Gln Val Gln Phe Lys
1               5                   10

<210> SEQ ID NO 12
<211> LENGTH: 11
<212> TYPE: PRT
<213> ORGANISM: Artificial
<220> FEATURE:
<223> OTHER INFORMATION: synthetic

<400> SEQUENCE: 12

Cys Ala Gln Gln Arg Pro Gln Val Gln Phe Lys
1               5                   10

<210> SEQ ID NO 13
<211> LENGTH: 11
<212> TYPE: PRT
<213> ORGANISM: Artificial
<220> FEATURE:
<223> OTHER INFORMATION: synthetic

<400> SEQUENCE: 13

Cys Arg Gln Gly Glu Pro Gln Val Gln Phe Lys
1               5                   10

<210> SEQ ID NO 14
<211> LENGTH: 10
<212> TYPE: PRT
<213> ORGANISM: Artificial
<220> FEATURE:
<223> OTHER INFORMATION: synthetic

<400> SEQUENCE: 14

Cys Ala Gly Glu Pro Gln Val Gln Phe Lys
1               5                   10

<210> SEQ ID NO 15
<211> LENGTH: 10
<212> TYPE: PRT
<213> ORGANISM: Artificial
<220> FEATURE:
```

<223> OTHER INFORMATION: synthetic

<400> SEQUENCE: 15

Cys Ala Gln Glu Pro Gln Val Gln Phe Lys
1               5                   10

<210> SEQ ID NO 16
<211> LENGTH: 10
<212> TYPE: PRT
<213> ORGANISM: Artificial
<220> FEATURE:
<223> OTHER INFORMATION: synthetic

<400> SEQUENCE: 16

Cys Ala Gln Gly Pro Gln Val Gln Phe Lys
1               5                   10

<210> SEQ ID NO 17
<211> LENGTH: 9
<212> TYPE: PRT
<213> ORGANISM: Artificial
<220> FEATURE:
<223> OTHER INFORMATION: synthetic

<400> SEQUENCE: 17

Cys Ala Gln Pro Gln Val Gln Phe Lys
1               5

<210> SEQ ID NO 18
<211> LENGTH: 9
<212> TYPE: PRT
<213> ORGANISM: Artificial
<220> FEATURE:
<223> OTHER INFORMATION: synthetic

<400> SEQUENCE: 18

Cys Gly Glu Pro Gln Val Gln Phe Lys
1               5

<210> SEQ ID NO 19
<211> LENGTH: 10
<212> TYPE: PRT
<213> ORGANISM: Artificial
<220> FEATURE:
<223> OTHER INFORMATION: synthetic

<400> SEQUENCE: 19

Ala Gln Gly Glu Pro Gln Val Gln Phe Lys
1               5                   10

<210> SEQ ID NO 20
<211> LENGTH: 9
<212> TYPE: PRT
<213> ORGANISM: Artificial
<220> FEATURE:
<223> OTHER INFORMATION: synthetic

<400> SEQUENCE: 20

Gln Gly Glu Pro Gln Val Gln Phe Lys
1               5

<210> SEQ ID NO 21
<211> LENGTH: 8
<212> TYPE: PRT
<213> ORGANISM: Artificial
<220> FEATURE:
<223> OTHER INFORMATION: synthetic -continued

```
<400> SEQUENCE: 21

Gly Glu Pro Gln Val Gln Phe Lys
1               5

<210> SEQ ID NO 22
<211> LENGTH: 4
<212> TYPE: PRT
<213> ORGANISM: Artificial
<220> FEATURE:
<223> OTHER INFORMATION: synthetic

<400> SEQUENCE: 22

Ala Gln Gly Glu
1
```

PEPTIDES AND NANOPARTICLE FORMULATIONS THEREOF

STATEMENT OF PRIORITY

This application is divisional application of U.S. patent application Ser. No. 16/096,947, which is a 35 U.S.C. § 371 national phase entry of International Application Serial No. PCT/GB2017/051222, filed May 2, 2017, which claims the benefit of Great Britain Application No. 1607593.9, filed Apr. 29, 2016, the disclosure of each of which is incorporated herein by reference in its entirety.

FIELD OF INVENTION

The present invention relates to a method for producing inhibitors of RanGDP and its specific guanine nucleotide exchange factor RCC1, peptide inhibitors of the RanGDP-RCC1 protein-protein interaction and the uses of these inhibitors in medicine. The invention also concerns nanoparticle formulations of the inhibitors and their use for the treatment of diseases associated with overexpression of the RAN gene.

BACKGROUND OF THE INVENTION

The term cancer relates to a family of diseases characterised by abnormal cell growth. The abnormal new growth of cells is referred to as a neoplasm. The cells in a neoplasm usually grow more rapidly than normal cells and will continue to grow if left treated. As they grow, neoplasms can impinge upon and damage adjacent structures, and can eventually compromise the survival of the host organism. Neoplasms can be benign or malignant (cancerous) and are often referred to as tumours. As used herein the term tumour is used to refer to malignant (cancerous) neoplasms. As a result, reference to the treatment of tumours and the treatment of cancer have the same meaning herein, while reference to breast cancer or breast tumour, and treatment thereof, refers to a cancer or tumour that originates in the breast, or treatment thereof, rather than a tumour that originates in another organ and that has spread to the breast through the process of metastasis. Tumours or cancers that originate in other organs or sites are referred to in a similar manner. Tumours that are derived from the process of metastasis are referred to as metastases or secondary tumours.

Hanahan and Weinburg ("The Hallmarks of Cancer". Cell 100 (1): 57-70) postulated that there are a number of traits or hallmarks that are common to the diseases known as cancer, namely (i) cancer cells stimulate their own growth; (ii) cancer cells resist inhibitory signals that might otherwise stop their growth; (iii) cancer cells resist their programmed cell death (they evade apoptosis); (iv) cancer cells can multiply indefinitely; (v) cancer cells stimulate the growth of blood vessels to supply nutrients to tumours (angiogenesis); and (vi) cancer cells invade local tissue and spread to distant sites (metastasis). Whether or not the full set of hallmarks, that have subsequently been supplemented ("Hallmarks of Cancer: The Next Generation" Cell 144 (5): 646-674), are exhibited by all cancers, it is apparent that by targeting these hallmarks affords an opportunity to exert a selective killing effect on cancer cells.

Cancer cells are addicted to oncogenes or oncogenic pathways (Weinstein, Science 2002; 297:63-4), which are usually uniquely present or hyperactivated, and are essential for tumour cell growth and survival. The two most frequently dysregulated signaling pathways in cancers are the phosphoinositide 3-kinase (PI3K)/Akt/mTORC1 and Ras/MEK/ERK [mitogen-activated protein/extracellular signal-regulated kinase (ERK; MEK)] pathways (Grant, J Clin Invest 2008; 118:3003-6). These growth signaling pathways usually exert their ultimate effect by regulating the translocation of transcription factors into or out of the nucleus, thereby altering the transcriptome and consequently, the expressome (Kau & Silver, Drug Discov Today 2003; 8:78-85). The activity of several oncogenic or tumour suppressive transcription factors, such as NF-kB, FOXO1, p53, and beta-catenin, and non-transcription factors, such as survivin, are regulated by their subcellular localization. Therefore, the uncoupling of nucleocytoplasmic transport from growth and survival signaling pathways has been suggested to be a potential target for cancer therapy.

Tumours or cancers are commonly referred to by the primary site of their occurrence, i.e. where the tumour first develops, and often also by reference to further characteristics, for example whether their growth is stimulated by hormones or whether they express certain receptors. Thus, primary tumours located in the breast are referred to breast cancers while tumours whose growth is stimulated by hormones such as estrogen, progesterone and testosterone are referred to as hormone dependent cancers. Breast cancers whose growth is stimulated by the presence of estrogen are known as estrogen receptor positive (ER+ve) breast cancers. This is important as a knowledge of the tumour characteristics indicates what therapeutic interventions are likely to be effective. For example, treatment of ER+ve tumours can involve estrogen deprivation, e.g. through blockage of estrogen biosynthesis with an aromatase inhibitor, or blocking of the signal derived from the interaction of an estrogen ligand with its receptor with a selective estrogen receptor modulator such as tamoxifen. These therapeutic interventions for the treatment of ER+ve tumours arrest the normal transcriptional activation of the estrogen receptor thereby blocking the estrogen stimulated growth of the tumour. Often, after presenting in an initial ER+ve state, breast cancer tumours progress to a hormone refectory state where their growth is independent of estrogen as, for example, through mutation, the estrogen receptor adopts a form in which it is transcriptionally activated even in the absence of estrogen, such tumours are also referred to as estrogen receptor negative (ER−ve) tumours. Similarly, breast cancers that express progesterone receptors and whose growth is sensitive to the presence of progesterone are referred to as progesterone positive (PR+ve) breast cancers whilst those whose growth is independent of the expression of progesterone receptor are progesterone receptor negative (PR−ve) breast cancers.

Another common sub-type of breast cancer is HER2-positive breast cancer, a subset of breast cancers that over express human epidermal growth factor 2. A number of HER2 targeted therapies have been developed, examples include the anti-HER2 antibodies trastuzumab and pertuzumab and the antibody-drug-conjugate trastuzumab emtansine.

Breast cancers that are negative for ER, PR and HER2, i.e. those tumour types whose growth is independent of ER, PR or HER2 status, are commonly referred to as triple negative breast cancers. Patients suffering from triple negative breast cancers presently have the worst overall and disease free survival rates. Treatment options for patients with triple negative breast tumours are relatively limited (Ontilo et al, Clin Med Res. 2009 June; 7(1-2): 4-13) with the present treatment paradigms usually involving a combination of surgery and radiation as appropriate with cytotoxic chemotherapy with agents such as anthracyclines, taxanes or platinum chemotherapeutic agents such as carboplatin unless the patient has the BRCA1 mutation. There is a clear need to deliver new therapies for use in the treatment of such conditions to improve the clinical prognosis for such patients (Andre & Zielinski, Ann Oncol (2012) 23 (suppl 6): vi46-vi51). It is an objective of the present invention to provide new therapies that are effective and are well tolerated for cancers such as triple negative breast cancer.

RAN, a member of the RAS Oncogene family is a gene that encodes the GTP-binding nuclear protein Ran. Overexpression of RAN gene is observed in a number of cancers and this overexpression has been linked to poor prognosis. For example, RAN overexpression has been shown to correlate with increased aggressiveness of cancer cells in vitro and in vivo (Kurisetty et al, Oncogene 2008, 27, 7139-49), i.e. RAN overexpressing cancer cells are seen to grow rapidly and exhibit high metastatic potential. Furthermore, in vitro studies have demonstrated that silencing the RAN gene with SiRNA or shRNA induces a greater degree of apoptosis in cancer cells relative to that induced in normal cells and in activated KRas-mutant cells relative to their isogenic K-Ras wild-type counterparts. Thus cancer cells are observed to be more sensitive to changes in RAN status than their normal counterparts. RAN silencing has also been observed to promote apoptosis in cancer cells with mutations that correlate with activation of the PI3K/Akt/mTORC1 and Ras/MEK/ERK signalling pathways (Yuen et al, Clin Cancer Res 2011; 18(2); 1-12). As result RAN has been suggested as a potential therapeutic target for cancer phenotypes in which the PI3K/Akt/mTORC1 and Ras/MEK/ERK pathways are activated.

Ran (Ras-related nuclear) protein, a 25-kDa protein encoded by RAN gene, is a G-protein GTPase that cycles between a GDP-bound (RanBDP) and a GTP-bound (RanGTP) state that regulates nucleocytoplasmic transport, mitotic spindle fibre assembly and post-mitotic nuclear envelope dynamics.

Ran exists in a different conformation depending on whether it is bound to GTP or GDP. In its GTP bound state, Ran is capable of binding karyopherins (importins and exportins) a set of proteins that are involved in importing and exporting molecules between the nucleus and the cytoplasm of a eukaryotic cell. Importins release a molecular cargo upon binding to RanGTP in the nucleus, while exportins must bind RanGTP in the nucleus to form a ternary complex with their export cargo in order to transport the cargo to the cytoplasm.

The dominant nucleotide binding state of Ran depends on whether it is located in the nucleus (RanGTP) or the cytoplasm (RanGDP), with RanGTP being formed inside the nucleus through interaction of Ran with its specific guanine nucleotide exchange factor (GEF), regulator of chromosome condensation 1 referred to herein as RCC1, which catalyses the exchange of GDP for GTP on the nucleotide binding pocket of Ran. Hydrolysis of RanGTP to RanGDP in the cytoplasm by RanGAP and RanBP1 releases energy and causes the ternary complex of Ran, exportin and cargo to dissociate thus releasing the cargo exported from the nucleus. Cytoplasmic RanGDP is in turn imported into the nucleus by the small protein NTF2 (Nuclear Transport Factor 2), where RCC1 can then catalyse exchange of GDP for GTP on Ran and complete the Ran cycle.

During mitosis, the Ran cycle is involved in mitotic spindle assembly and nuclear envelope reassembly after the chromosomes have been separated. During prophase, the steep gradient in RanGTP-RanGDP ratio at the nuclear pores breaks down as the nuclear envelope becomes leaky and disassembles. RanGTP concentration stays high around the chromosomes as RCC1 stays attached to chromatin as the nucleoporin RanBP2 (Nup358) and Ran GTPase activating protein (RanGAP) move to the kinetochores where they facilitate the attachment of spindle fibres to chromosomes. Moreover, RanGTP promotes spindle assembly by mechanisms similar to mechanisms of nuclear transport: the activity of spindle assembly factors such as NuMA and TPX2 is inhibited by the binding to importins. By releasing importins, RanGTP activates these factors and therefore promotes the assembly of the mitotic spindle. In telophase, RanGTP hydrolysis and nucleotide exchange are required for vesicle fusion at the reforming nuclear envelopes of the daughter nuclei.

It is an object of the present invention to provide a new therapeutic strategy for the treatment of cancer by targeting Ran. To this end the present invention provides a method of generating peptide inhibitors of the Ran-RCC1 protein/protein interaction, peptide inhibitors of the Ran-RCC1 protein/protein interaction, and use of these new inhibitors in medicine, for example in the treatment of cancer, and in particular cancer phenotypes in which the PI3K/Akt/mTORC1 and Ras/MEK/ERK pathways are activated. Diseases overexpressing Ran include but are not limited to certain breast, lung, prostate, ovarian, blood, brain and renal cancers and include those cancers currently associated with poor patient prognosis such as triple negative breast cancer.

SUMMARY OF THE INVENTION

In a first aspect of the invention there is provided a method for the preparation of a peptide inhibitor of the RanGDP-RCC1 protein/protein interaction comprising the steps of:

i) identifying segments of the Ran protein sequence (SEQ ID NO: 1) predicted to interact with RCC1 in the formation or stabilisation of the RanGDP-RCC1 complex; and ii) preparing a 6 to 25 amino acid peptide with a sequence comprising a contiguous sequence of at least 6 amino acids corresponding to a portion of one of the segments of Ran identified in step i)

wherein the peptide optionally has a cysteine residue not present in the corresponding segment of Ran at its N-terminus, and wherein, not counting the optional cysteine residue at the N-terminus, the peptide has at least 80% homology with a portion of one of the segments of Ran identified in step i) or has not more than 2 point deletions or mutations relative to a portion of one of the segments of Ran identified in step i).

In one embodiment the method of the invention provides a peptide that is 90% or 100% homologous with a portion of one of the segments of Ran identified in step i).

In one embodiment the segments of Ran identified in step i) is selected from MAAQGEPQVQFKLVLVGDG (SEQ ID NO: 2); RKVKAKSIVFHRKK (SEQ ID NO: 3); or PALAAQYEHDLEVAQTTALP (SEQ ID NO: 4).

In one embodiment the segment of Ran identified in step i) is MAAQGEPQVQFKLVLVGDG (SEQ ID NO: 2).

In one embodiment the peptide product of the method is from 8 to 20 or 10 to 20 amino acids in length. In one embodiment the peptide product of the method is from 11 to 15 amino acids in length, for example 11, 12, 13, 14 or 15 amino acids in length.

In another aspect the invention provides a peptide consisting of from 6 to 25 amino acids comprising the amino acid sequence $(X)_m$—Y wherein: X=Cys; m=0 or 1; and Y comprises an amino acid sequence comprising a contiguous sequence of 6 amino acids present in MAAQGEPQVQFKLVLVGDG (SEQ ID NO: 2); RKVKAKSIVFHRKK (SEQ ID NO: 3); or PALAAQYEHDLEVAQTTALP (SEQ ID NO: 4) further wherein a) Y is sequence having at least 80% homology to a portion of the sequence of SEQ ID NO: 2, SEQ ID NO: 3, or SEQ ID NO: 4 containing the same number of amino acids; or b) Y is a sequence corresponding to a portion of SEQ ID NO: 2, 3, or 4 having not more than 2 point deletions or mutations; or a pharmaceutically acceptable form thereof.

In one embodiment the peptide according to the invention has a group Y that is 90% or 100 homologous to a portion of SEQ ID NO: 2, 3 or 4 containing the same number of amino acids.

In one embodiment the peptide according to the invention has a group Y that is 80, 90% or 100% homologous to a portion of SEQ ID NO: 2 and the integer m=1. In one embodiment the peptide according to the invention has a group Y that contains a Ala-Gln-Gly-Glu (AQGE) motif and is 80, 90% or 100% homologous to a portion of SEQ ID NO: 2 and the integer m=1.

In one embodiment the peptide according to the invention has the structure SEQ ID NO: 5, SEQ ID NO: 6 or SEQ ID NO:7.

In a further aspect the invention relates to a nanoparticle formulation comprising a peptide according to the invention or an inhibitor of RanGDP-RCC1 optionally obtained from the method of the invention.

In a further aspect the invention relates to an inhibitor of the RanGDP-RCC1 protein-protein interaction for use in medicine.

In one embodiment the inhibitor of the RanGDP-RCC1 interaction for use in medicine is a peptide inhibitor of the RanGDP-RCC1 interaction obtained according to the method of the invention or a peptide according to the invention.

In a further aspect the invention provides use of a peptide according to the invention or a pharmaceutically acceptable form thereof for the manufacture of a medicament, optionally wherein the medicament is for the treatment of cancer.

In a further aspect the invention provides a method of treatment for a patient in need thereof comprising the step of administering an inhibitor of the RanGDP-RCC1 protein-protein interaction, optionally wherein the patient has cancer.

DESCRIPTION OF DRAWINGS

In order that the invention can be fully understood, the invention and embodiments thereof are described with reference to the following Figures, which are not intended to limit the scope of the invention.

DETAILED DESCRIPTION OF THE INVENTION

Figure 1:
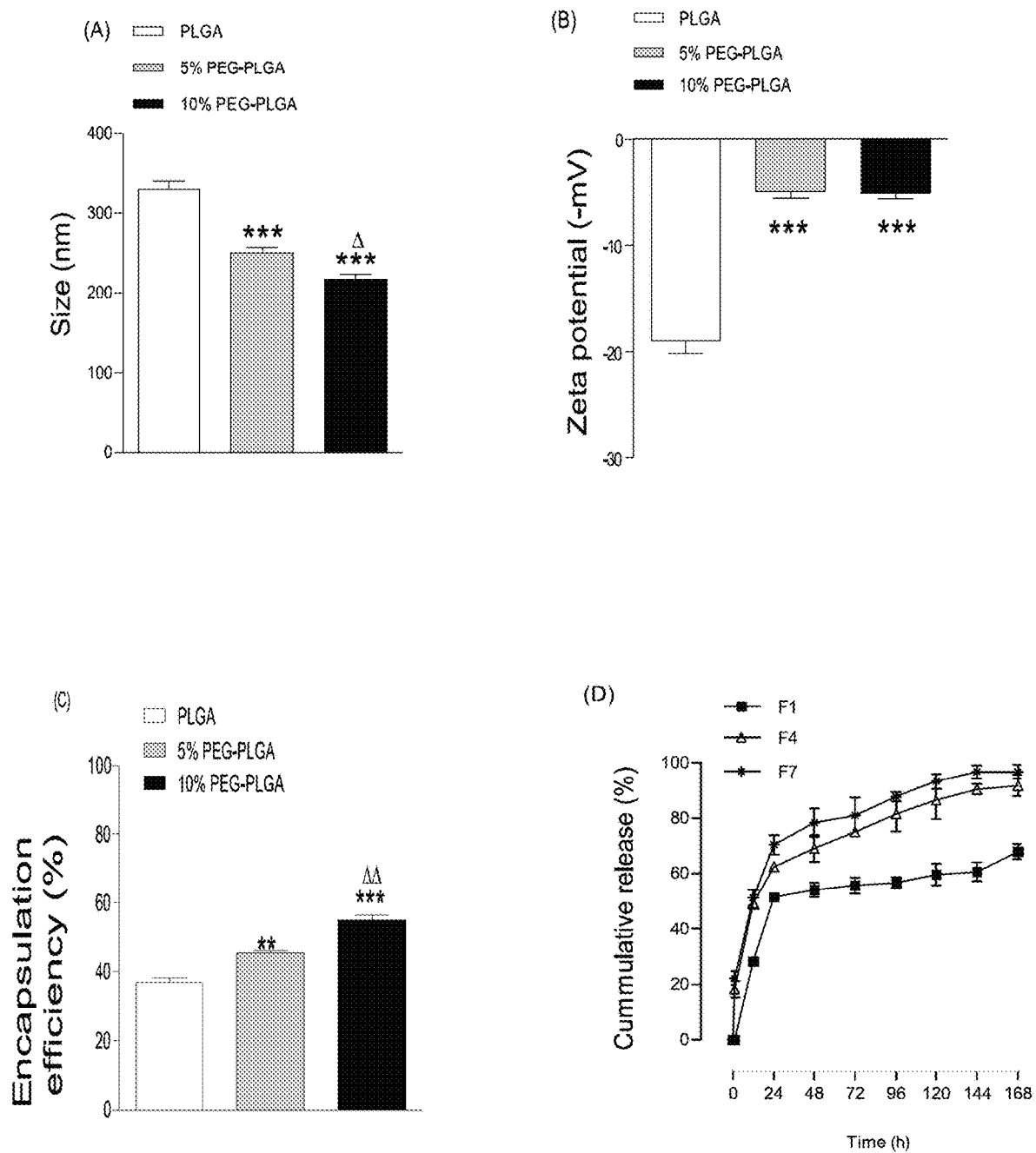
FIG. 1 illustrates the effects of polymer type on (panel A) nanoparticle of containing peptide of SEQ ID NO: 5 on size, (panel B) zeta potential, (panel C) encapsulation efficiency and (panel D) in vitro release peptide. Values are mean±SD with n=3. For FIG. 1, panels A-C, $*p<0.05$, $p<0.01$, $*p<0.001$ compared with PLGA. $^{\Delta}p<0.05$ compared with 5% PEG-PLGA.

Ran is a member of the Ras superfamily that regulates nucleocytoplasmic transport, mitotic spindle fibre assembly and post-mitotic nuclear envelope dynamics. Ran acts as a molecular switch through a GTP-GDP cycle in which the conversion between GTP-bound and GDP-bound conformations controls its interaction with different effectors. RanGTP is formed inside the nucleus by interaction of Ran with its specific guanine nucleotide exchange factor (GEF), referred to herein as RCC1, which catalyses the exchange of GDP for GTP (and vice versa) on the nucleotide binding pocket of Ran. The present invention relates to methods of producing peptide inhibitors of the binding of RCC1 in the RCC1 specific binding pocket of RanGDP. The invention further relates to disruption of the normal interaction between Ran-GDP and RCC1 with peptides that competitively inhibit the binding of RCC1 in the RCC1 specific binding pocket of RanGDP. The invention also relates to inhibitors of RanGDP-RCC1 protein-protein interaction for use in medicine and in particular for the treatment of cancer and advantageous formulations of these inhibitors.

RanGDP-RCC1 Inhibitors and Methods of Preparing the Same

In a first aspect of the invention there is provided a method for the preparation of a peptide inhibitor of the RanGDP-RCC1 protein/protein interaction comprising the steps of:

i) identifying segments of the Ran protein sequence (SEQ ID NO: 1) predicted to interact with RCC1 in the formation or stabilisation of the RanGDP-RCC1 complex; and ii) preparing a 6 to 25 amino acid peptide with a sequence comprising a contiguous sequence of at least 6 amino acids corresponding to a portion of one of the segments of Ran identified in step i), wherein the peptide optionally has a cysteine residue not present in the corresponding segment of Ran at its N-terminus, and wherein, not counting the optional cysteine residue at the N-terminus, overall the peptide has at least 80% homology with a portion of one of the segments of Ran identified in step i) or has not more than 2 point deletions or mutations relative to a portion of one of the segments of Ran identified in step i).

The present inventors have identified three sites of interest for the generation of peptide inhibitors of the RanGDP-RCC1 interaction. These sites are identified on the basis of knowledge of the secondary structure of the Ran protein (SEQ ID NO:1) and that obtained from protein crystallography of the complex between Ran and RCC1 and biochemical studies of the Ran-RCC1 interaction e.g. the influence of mutations on complex formation and RCC1 catalysed GDP-GTP exchange kinetics. For example, a knowledge of the secondary structure of Ran and the effects of mutation studies provides an insight on which fragments of Ran are involved in the formation and function of the RanGDP-RCC1 complex. This is because the formation of the RanGDP-RCC1 complex is a dynamic process and involves various interactions that are not observed in the static pictures provided by X-ray crystallography. In other words, the motifs of the secondary structure of Ran that are not in close proximity to RCC1 in the Ran-RCC1 protein crystal structure can make a significant contribution to the kinetics of Ran-RCC1 complex formation and can thus represent significant targets for inhibitors.

Protein crystallography of the Ran-RCC1 interaction, for example the protein crystal structure 1i2m, provides details on a frozen complex between the two macromolecules and allows identification of residues on each protein that are sufficiently close (within 3.5 Å), that they contribute a positive energy contribution to binding. The interactions between the two protein can involve for example hydrogen bonds, pi-stacking or hydrophobic interactions. Computational analysis therefore allows identification of those amino acid residues of Ran outside the GDP/GTP binding site of Ran that can bind to RCC1. Applying this information an in silico design process involving selection of fragments of the natural amino acid sequence of Ran from 4 to 25 amino-acids in length were generated in silico and their interaction with RCC1 was evaluated with a virtual docking approach. Peptides with the best scores were then synthesised by conventional techniques and evaluated for activity on the target. This approach delivered a predictable method for the generation of peptide inhibitors of the Ran-RCC1 interaction that are fragments of the natural Ran protein. It was found that adding a cysteine residue at the N-terminus of the peptide fragments identified was advantageous in that the resultant peptides were more soluble and therefore better suited for direct therapeutic application. Addition of this cysteine residue was not found to have any significant adverse effects on RanGDP-RCC1 inhibition. Best scores were obtained with peptide sequences with eight or more amino acid residues.

The protein crystal structure of Ran-RCC1 reveals that on complex formation, the proteins Ran and RCC1 bury a large solvent-accessible surface area of approximately 2700 A°. Twenty-four residues of Ran and 25 residues of RCC1 can be seen from the structure of 1 i2m to be involved in contact formation. The sites at which Ran interacts with its RCC1 are concentrated around the P loop (residues 19 to 20), Switch II (residues 67 to 76), and helices a3 (residues 93 to 110) and a4 (residues 134, 137, and 140). In designing inhibitors, computational analysis revealed that the secondary protein structure around the P loop and towards the N-terminus including the turn (residues 2 to 5) and strand (residues 10 to 17) the region around □4 helices (in the region of residues 129 to 142) to be of particular interest.

The co-crystal structure of Ran-RCC1 also revealed a difference between Ran and the other members of the Ras superfamily, namely the presence of a long C-terminal extension that ends in a conserved C-terminal DEDDDL motif (residues 211 to 216). In Ran, the C-terminal region adjacent to the DEDDDL motif consists of a linker and a helix (residues 191 to 205) situated opposite a switch region of the protein. Biochemical and structural studies have shown that this C-terminal switch is detached from the G domain and is flexible in the GTP-bound state. In the Ran RCC1 complex, the Ran protein residues from 178 onward are largely disordered. In the region anchoring the C-terminal end onto the G domain, large conformational changes are observed compared to RanGDP and RanGTP structures. Thus although RCC1 does not appear itself to directly interact with the C-terminus of Ran in the Ran-RCC1 protein crystal structure, RCC1 appears to interact with residues in the 129-142 region of Ran such that a clash of RCC1 with Lys130, repositions residues 129-142 of Ran such that they would sterically interfere with the C-terminal helix in RanGDP, in turn leading to the release of the C terminus from the G domain core. It was thus identified that RCC1 could have an active role in inducing the C-terminal switch and this is supported by in vitro experiments that show that RCC1-catalyzed GDP release is significantly faster with a $\Delta^{211}$DEDDDL Ran mutant. The present inventors have shown that for Ran the G19V mutation inhibits the RCC1-catalyzed GDP to GTP exchange reaction and thus identified a potential region for interference with the RanGDP-RCC1 interaction. When studying interactions in this region the AQGE residues that overlap with the turn at residues 2 to 5 of Ran (SEQ ID NO: 1) appeared to be especially significant for inhibition.

The above insights led the inventors to assess peptide fragments spanning, at least in part, i) the N-terminal region of Ran (i.e. residues 1 to 19 of Ran); ii) the C-terminal region of Ran without GTP consensus sequence DEDDDL (i.e. residues 191-210 of Ran); and iii) residues of Ran around the □4 helices identified as rich in residues interacting with RCC1 in the protein crystal structure 1i2m (i.e. residues 129 to 142 of Ran); as inhibitors of the binding of RanGDP to RCC1. Data obtained for three inhibitors of the RanGDP-RCC1 targeting these areas (SEQ ID Nos: 5, 6, and 7) validated this analysis and support a general approach for the generation of peptide inhibitors of the RanGDP-RCC1 involving taking a highly conserved fragments of the protein sequence in these three areas being at least 8 amino acids in length and having either 80% or more homology with the fragment of the Ran sequence in the identified area or corresponding to the natural sequence of Ran in the identified with not more than two deletions. The process according to the invention therefore allows new inhibitors of the Ran-RCC1 interaction to be generated in a predictable manner based solely on a structural and biochemical knowledge of Ran, the RanGDP-RCC1 complex.

In preferred embodiments the sequences identified in step i) of the method of the invention are selected from any of SEQ ID Nos: 2, 3 and 4. This method allows the identification of competitive inhibitors of the RanGDP-RCC1 protein-protein interaction and thus affords direct access to peptide compounds that can be used directly, or in a pharmaceutically acceptable form, to inhibit the normal interaction of RanGDP and RCC1. The peptide products of the process can potentially be used in medicine.

In one embodiment the peptide product of the method of the invention features a cysteine residue at its terminus. Incorporation of the cysteine residue at the N-terminus can advantageously improve the solubility of the peptide inhibitor and is thus advantageous for direct administration as a medicine or further transformation into an alternative pharmaceutically acceptable form such as a prodrug or conjugation to an alternative delivery system such as a nanoparticle or an antibody. For example, it is envisaged that the inhibitors of the invention could be administered in any pharmaceutically acceptable form, for example in the form of an antibody-drug conjugate or conjugated to a nanoparticle delivery system.

In one embodiment the peptide product of the method of the invention is from 8 to 20 amino acids in length. In one embodiment the peptide product of the method of the invention is from 10 to 20 amino acids in length. In one embodiment the peptide product of the method of the invention is from 11 to 15 amino acids in length. It can be important to balance the length of the peptide inhibitor that generally confers higher affinity to the target with the need for efficient delivery of a peptide drug to its site of action that can sometime be compromised when the peptide is too long.

The peptide inhibitors of the present invention can be prepared by methods well known to those skilled in the art. Standard peptide synthesis, as used in the present method, involves use of suitably protected forms of the relevant amino acids, linking the C-terminus carboxyl of a first amino acid (or peptide fragment), usually protected at its N-terminus to avoid dimerization, with the N-terminal amino group of a second amino acid (or peptide fragment) with a peptide coupling reaction to form an amide bond between the first and second amino acids (or peptide fragments) to form a dipeptide (or large peptide if one or more of the starting materials are peptide fragments). The N-terminus of the product peptide can then be deprotected to form the starting material for a second cycle of amide bond formation followed by deprotection. Once the peptide chain has reached the desired length the protecting groups from both the N- and C-termini are removed to afford the desired product. Peptide synthesis can be performed in the liquid phase or in the solid phase as desired. The solid phase advantageously allows the process to be automated as the purification involves a simple washing step in which non-bound byproducts or reagents are removed by washing or filtration. Protecting groups for the N-terminal amino group are typically carbamates such as Fmoc and Boc groups although a range of alternative groups exist. If side chain protecting groups are required, for example when an amino acid with a reactive side chain group is present in the sequence, for example the thiol group of cysteine, the hydroxyl group of serine or the carboxylic acid of glutamic acid, then protecting groups such as benzyl derivatives or t-butyl can be used. Amide bond forming reactions are typically catalysed with reagents such as DIC, PyBOP, DEPBT, HATU, HBTU that are used in combination with a base such as Hunig's base (N,N-diisopropylethylamine). Solid supports commonly used include polystyrene resin, polyamide resin and PEG based resin or hybrid resins such as tentagel. Standard deprotecting reagents such as trifluoroacetic acid (for Boc) and piperidine (for Fmoc) or well known alternatives thereof can be selected as appropriate. Cleavage reagents used to remove the peptide from its solid support are also well known and depend on the solid support that is used. The solid support can be selected from any system known in the art.

The method of the invention thus provides direct access to peptide inhibitors of the RanGDP-RCC1 interaction. These inhibitors of the RanGDP-RCC1 interaction are suitable for use in medicine, for example, be used in the treatment of a condition that is characterised by upregulation of RAN gene. One such condition that inhibitors of the RanGDP-RCC1 interaction is cancer, for example a cancer in which the RAN gene is overexpressed. In one embodiment the peptide inhibitors produced by the method of the invention are from 8 to 25 amino acids in length. Peptide inhibitors from 10 to 15 amino acids in length are particularly preferred. It preferred that the peptide inhibitors have at least 80% or 90% with a portion of one of the segments of Ran identified in step i) of the method of the invention. In some preferred embodiments the peptide inhibitor produced by the method of the invention has an amino acid sequence identical to portion of one of the segments of Ran identified in step i).

In one embodiment the invention provides a peptide inhibitor of the RanGDP-RCC1 interaction. The peptide inhibitors according to the invention are competitive inhibitors of the interaction between Ran and RCC1 within the RCC1 binding pocket of RanGDP. These inhibitors work by binding to RCC1 directly and thus block the formation of the RanGDP-RCC1 complex. Blockage of the RanGDP-RCC1 complex arrests the transport of RanGDP from the cytoplasm back into the cell nucleus and consequently the regeneration of RanGTP in the nucleus. As a result of this inhibition of the normal Ran cycle, that plays a key role in mitotic spindle assembly and nuclear envelope reassembly after the chromosomes have been separated during the process of mitosis (cell division), the inhibitors of RanGDP-RCC1 according to the invention can be used in medicine. In particular, the peptide inhibitors of the RanGDP-RCC1 can be used to for the treatment of conditions that overexpress the RAN gene. Certain cancer types, for example certain breast, lung, ovarian, blood, brain and renal cancers, including cancers currently associated with poor patient prognosis such as triple negative breast cancer may well be treatable by use of the peptide inhibitors according to the invention. The inhibitors of RanGDP-RCC1 according to the invention are suitable for the treatment of solid tumours and leukaemias (blood cancers).

In one embodiment the peptide inhibitors according the invention comprise an amino acid sequence that is identical to a 6 amino acid portion of the residues 1 to 19 of the N-terminal region of Ran (SEQ ID No: 2) optionally terminating with a cysteine residue. The region around the N-terminus of Ran has a secondary structure comprising a turn at positions 3 to 5, beta strands at positions 10 to 17 and 18 to 22 and helices at positions 23 to 27 and 31 to 35. Applying the method of the invention it was determined that a 10 amino acid sequence homologous to the amino acids of positions 3 to 12 of Ran would effectively inhibit the interaction of Ran with RCC1 within the RCC1 binding pocket of RanGDP. This sequence, with a Cys residue on its N-terminus, CAQGEPQVQFK (SEQ ID NO: 5), was thus prepared and evaluated for activity. The results obtained with the peptide of SEQ ID NO: 5 are described below and are illustrated in the figures.

In preferred embodiments the peptide inhibitors of the invention that have high homology with the N-terminal domain of Ran contain the amino acid sequence AQGE that is found at residues 3 to 6 of the natural peptide. Results obtained from deletion experiments suggest that the AQGE fragment confers particularly good inhibitory activity of the RanGDP-RCC1 interaction. Accordingly, peptide inhibitors of the invention targeting the N-terminal region (SEQ ID NO: 2) preferably possess this AQGE motif in their overall structure.

In one embodiment the peptide inhibitors according the invention comprise an amino acid sequence that is identical to a 6 amino acid portion of the residues 129 to 142 of the central region of Ran (SEQ ID NO: 3) optionally terminating with a cysteine residue. The region in the centre of Ran has a secondary structure comprising beta strands at positions 112-114, 117 to 122 and 126-128 and helices at positions 133 to 135 and 138 to 142. Applying the method of the invention it was determined that a 12 amino acid sequence homologous to the amino acids of positions 124 to 135 of Ran would effectively inhibit the interaction of Ran with RCC1. This sequence, CVDIKDRKVKAKS (SEQ ID NO: 6), was thus prepared with a Cys residue on its N-terminus for and evaluated for activity. The results obtained with the peptide of SEQ ID NO: 6 are described below and are illustrated in the figures.

In one embodiment the peptide inhibitors according the invention comprise an amino acid sequence that is identical to a 6 amino acid portion of the residues 191 to 210 located in the C-terminal region of Ran (SEQ ID No: 4) optionally terminating with a cysteine residue. The region around the C-terminus of Ran has a secondary structure comprising a turn positions 185 to 187 and helices at positions 191 to 205 and 211 to 215. Applying the method of the invention it was determined that a 14 amino acid sequence homologous to the amino acids of positions 196 to 210 of Ran would effectively inhibit the interaction of Ran with RCC1. This sequence with a Cys residue on its N-terminus CQYEHDLEVAQTTALP (SEQ ID NO: 7) was thus prepared and evaluated for activity. The results obtained with the peptide of SEQ ID NO: 7 are described below and are illustrated in the figures.

As well as having peptide inhibitors with sequences that are completely homologous with fragments of Ran identified as site of interest for inhibitor development (i.e. SEQ ID NOs: 2, 3 and 4), it is anticipated that peptide sequences according to the invention with 80% or 90% homology with the corresponding fragment of the natural peptide may display sufficient inhibitory activity to be therapeutically useful. Likewise, peptide sequences corresponding to fragments of the inhibitory peptide corresponding to fragments of Ran identified as site of interest for inhibitor development (i.e. SEQ ID NOs: 2, 3 and 4) having not more than 2 point deletions or mutations relative to a portion of one of e.g. SEQ ID NOs: 2, 3 and 4 are also believed to possess significant therapeutic potential.

Examples of sequences generated by one or two point mutations according to the invention are provided below with the site of mutation underlined. Similar point mutations on the other sequence according to the invention will be apparent to those skilled in the art based on the knowledge of how such mutation can be used to modulate peptide inhibitor activity in the common general knowledge.

```
                                          (SEQ ID NO: 5)
         CAQGEPQVQFK (SEQ ID NO: 8)
         CEQGEPQVQFK (SEQ ID NO: 9)
         CASGEPQVQFK (SEQ ID NO: 10)
         CAQMEPQVQFK (SEQ ID NO: 11)
         CAQGFPQVQFK (SEQ ID NO: 12)
         CAQQRPQVQFK (SEQ ID NO: 13)
         CRQGEPQVQFK
```

Examples of sequences generated by deletion of residues from SEQ ID NO 5 are shown below alongside SEQ ID NO: 5 that is shown for ease of reference. Similar point mutations on the other sequence according to the invention will be apparent to those skilled in the art based on the knowledge of how such mutation can be used to modulate peptide inhibitor activity in the common general knowledge.

```
         (SEQ ID NO: 5)
         CAQGEPQVQFK (SEQ ID NO: 14)
         CAGEPQVQFK (SEQ ID NO: 15)
         CAQEPQVQFK (SEQ ID NO: 16)
         CAQGPQVQFK (SEQ ID NO: 17)
         CAQPQVQFK (SEQ ID NO: 18)
         CGEPQVQFK (SEQ ID NO: 19)
         AQGEPQVQFK (SEQ ID NO: 20)
         QGEPQVQFK (SEQ ID NO: 21)
         GEPQVQFK
```

Figure 10:
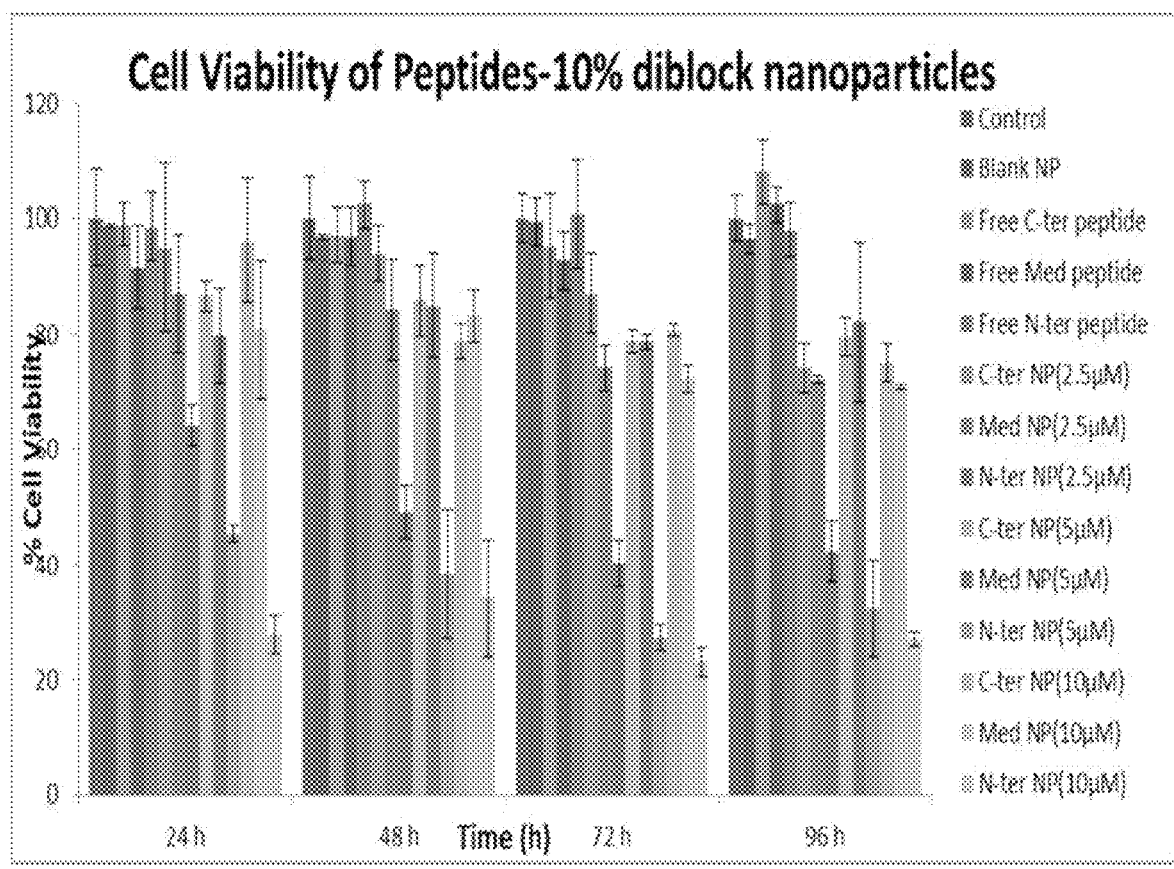
FIG. 10 shows MDA-MB-231 breast cancer cell viability after treatment with peptides of SEQ ID NO: 7 (C-ter peptide), SEQ ID NO: 6 (Med) and SEQ ID NO: 5(N-ter) in free and nanoparticle (NP) forms alongside control and unloaded nanoparticle (NP) treated cells.
Figure 11:
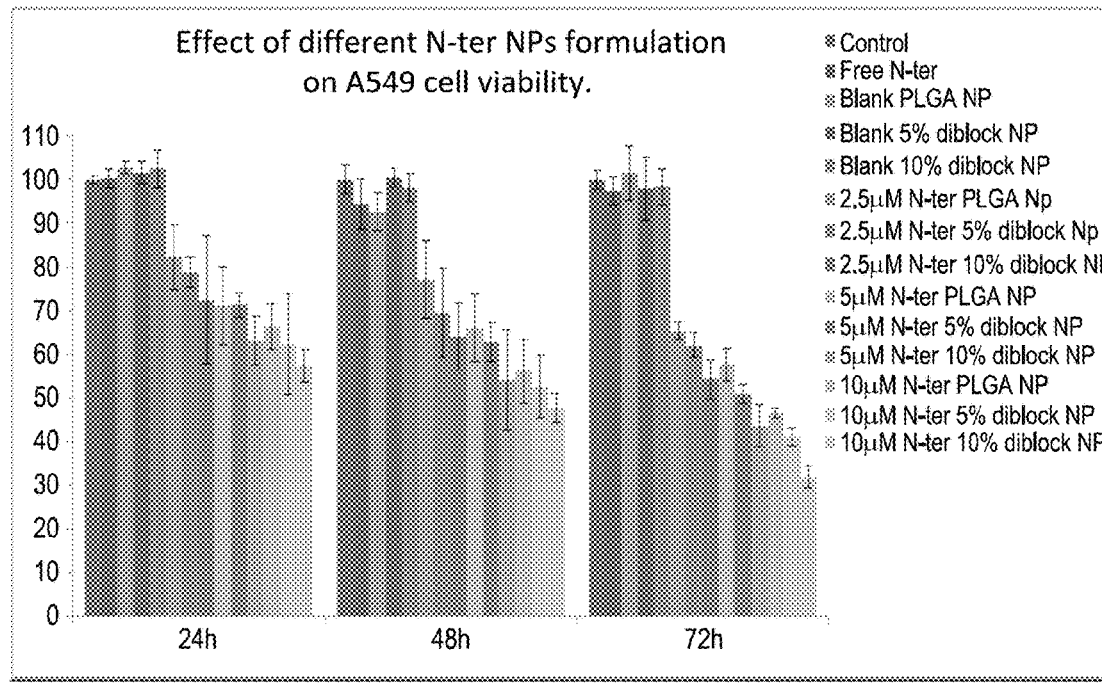
FIG. 11 shows A549 lung cancer cell viability after treatment with peptides of SEQ ID NO: 7 (C-ter peptide), SEQ ID NO: 6 (Med) and SEQ ID NO: 5 (N-ter) in free and nanoparticle (NP) forms alongside control and unloaded nanoparticle (NP) treated cells.

As can be seen from the data in FIGS. 10 and 11 the peptide inhibitors SEQ IDs 5, 6 and 7 all display significant activity against the proliferation of MDA MB-231 triple negative breast cancer cells and A549 lung cancer cells in vitro when dosed as nanoparticles. These cells lines demonstrate activity against relevant human tumour cell lines and are commonly accepted as being a first line indicator of therapeutic activity in vivo and, ultimately, potential clinical application.

Figure 12:
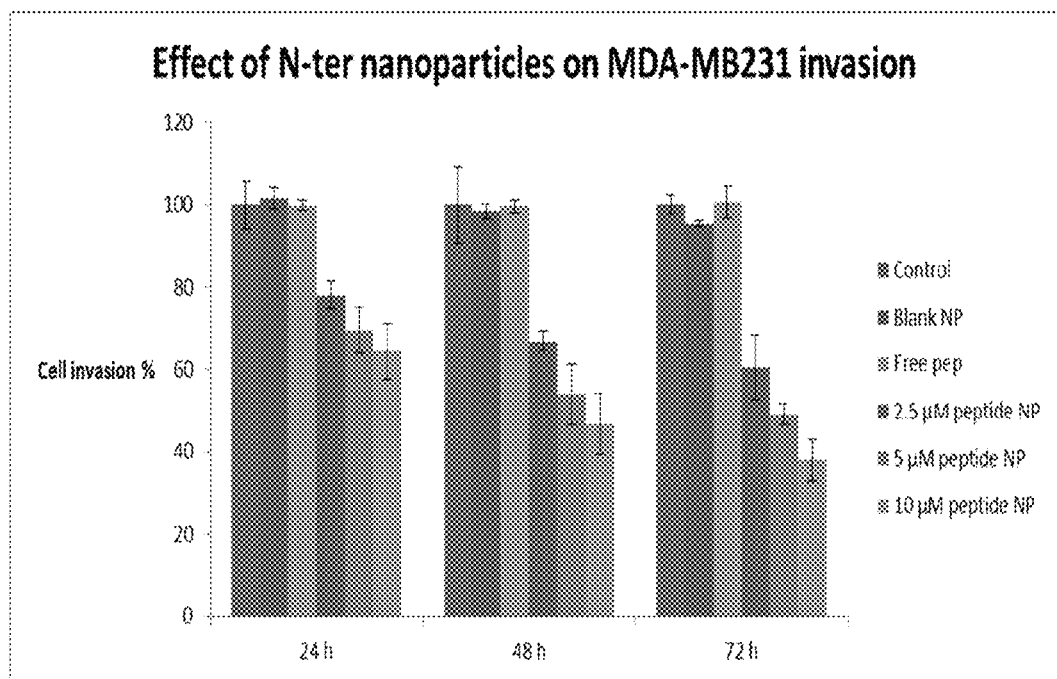
FIG. 12 shows the inhibitory effect of SEQ ID NO: 5 (N-ter) loaded nanoparticles on MDA-MB231 invasion.
Figure 13:
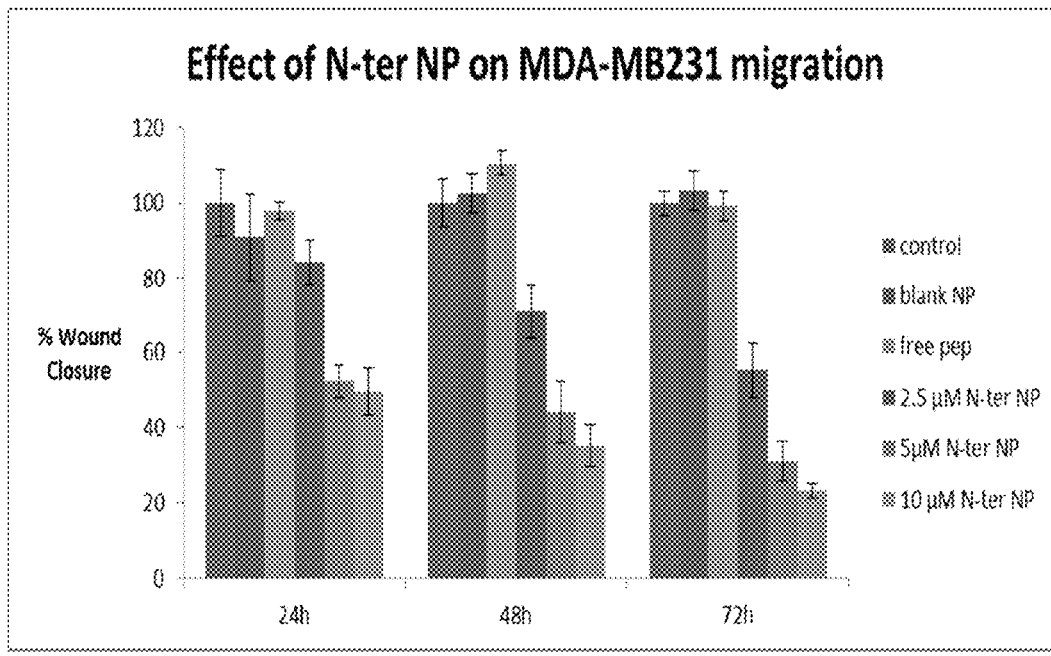
FIG. 13 shows the inhibitory effect on SEQ ID NO: 5 (N-ter) loaded nanoparticles on MDA-MB231 migration.

Furthermore, FIGS. 11 and 12 provide data on the cell invasion and migration observed for MDA MB-231 cells observed after treatment with peptide of SEQ ID NO: 5. This data suggest that in addition to inhibiting cell proliferation inhibiting the RanGDP-RCC1 interaction can reduce the aggressiveness of treated cells and significantly their metastatic potential.

Figure 14:
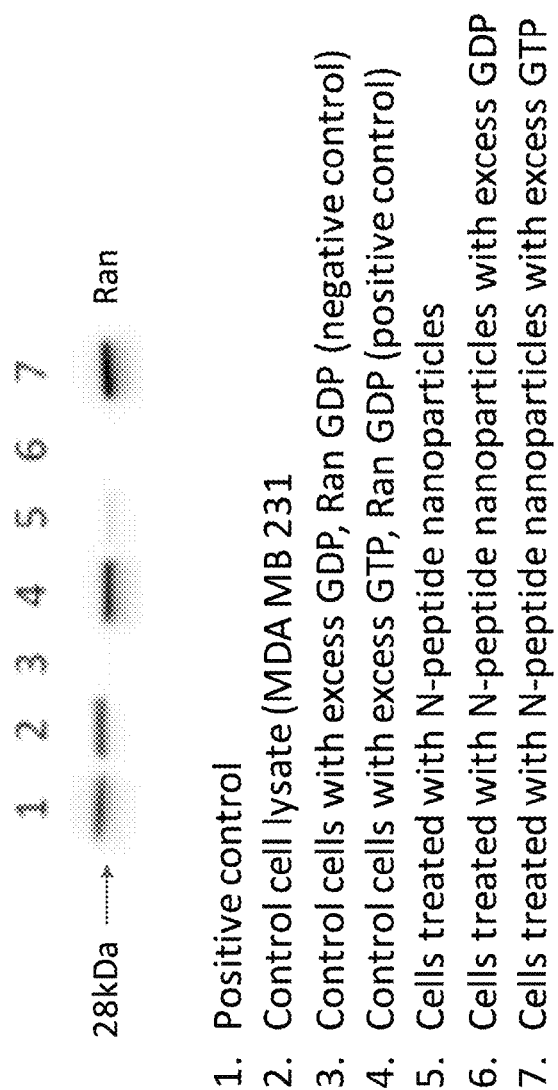
FIG. 14 shows the results of a Ran activation assay that demonstrates direct activity of a peptide inhibitor of SEQ ID NO: 5 on the RanGDP-RCC1 protein-protein interaction.

FIG. 14 displays results obtained in a Ran-activation assay. Lane 1 is positive control for activated Ran complex & Lane 2, MDA MB-231 cell lysate, Lane 3 MDA MB-231 cell lysate loaded with GDP and incubated (negative control) with RanBP1 Agarose beads. Lane 4, MDA MB-231 cell lysate loaded with GTPyS (positive control) incubated with RanBP1 Agarose beads. Lane 5, MDA MB231 cell lysate treated by N-Terminal peptide, Lane 6, MDA MB-231 cell lysate loaded with GD and treated with N-terminal peptide SEQ ID NO: 5, Lane 7, MDA MB231 cell lysate loaded with GTPyS and treated with N-terminal peptide SEQ ID NO: 5 incubated with RanBP1 Agarose beads. This experiment shows that the peptide of SEQ ID NO: 5 disturbs the interaction between Ran-GDP and RCC1 (compare Lane 2 with Lane 5) in native cells because addition of the inhibitor knocks down the protein level. This experiment also shows that N-terminal peptide disturbs the interaction between Ran-RCC1 away from GTP binding pocket (compare lanes 4 & 7). It can therefore be seen that the N-terminal peptide SEQ ID NO: 5 disturbs the interaction between Ran-RCC1 by direct binding to RCC1.

Figure 15:
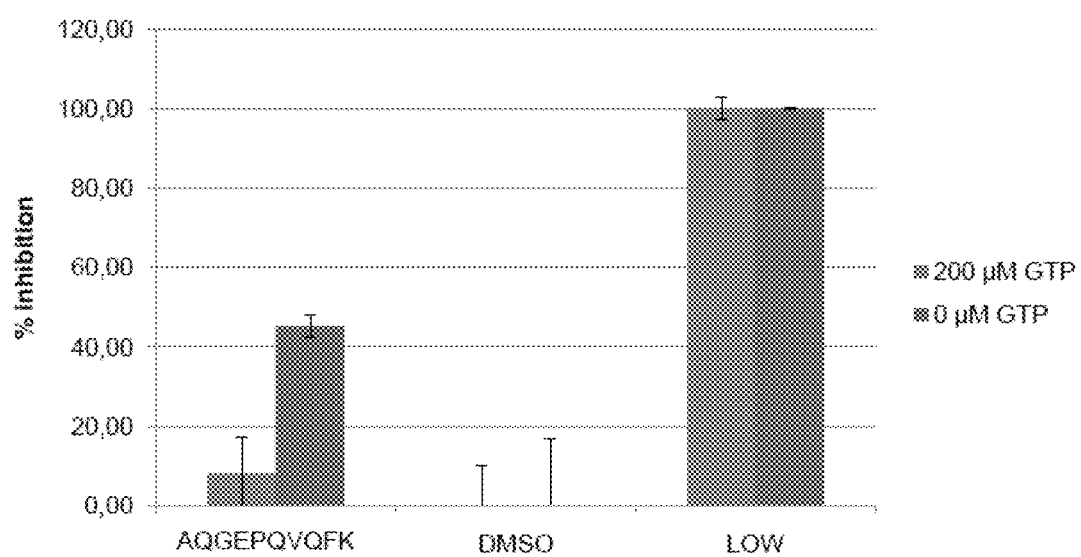
FIG. 15 shows the results of an AlphaScreen™ assay indicating the inhibitor of SEQ ID NO: 5 directly inhibits the RanGDP-RCC1 protein-protein interaction.

The direct effect of the inhibitor of SEQ ID NO: 5 on the RanGDP-RCC1 interaction was also studied by AlphaScreen™ assay. This assay employs bead-based chemistry used to study biomolecular interactions in a microplate format, the acronym ALPHA stands for Amplified Luminescent Proximity Homogeneous Assay. In brief, the system uses two photosensitive bead types, a first donor bead that can absorb light from an external light source and a second acceptor bead that can first absorb energy from the donor bead if the beads are in close proximity and then in turn emit light. The Ran protein was attached to the donor bead and the RCC1 protein was attached to the acceptor bead. In the absence of peptide inhibitor the interaction of Ran and RCC1 hold the beads in close proximity and the emission from the acceptor bead is detectable. In the presence of the inhibitor of SEQ ID NO: 5 the emission form the acceptor bead was substantially reduced indicating that the inhibits according to the invention directly target the Ran-RCC1 interaction. As can be seen from FIG. 15, a 45% inhibition of complex formation was observed in the absence of GTP.

The results of the Ran activation assay and the AlphaScreen™ assay strongly support the activity on cell lines in e.g., FIGS. 10-13 being attributable to the inhibition of the RanGDP-RCC1 protein-protein interaction. This proof of principle provides convincing evidence of the potential use of inhibitors of the RanGDP-RCC1 protein-protein interaction in medicine and in particular in the treatment of cancer, such as triple negative breast cancer (MDA MB-231 cells are triple negative human breast cancer cells).

Medicament/Methods of Treatment

It is an aspect to provide inhibitors of the RanGDP-RCC1 interaction as defined according to the present invention for use as a medicament.

In another aspect, the present invention provides methods for treatment or alleviation of cancer in the tissue of one or more organs as mentioned herein. Such methods according to the present invention in one embodiment comprise one or more steps of administration or release of an effective amount of a peptide according to the present invention, or a pharmaceutical composition comprising one or more such peptides, to an individual in need thereof. In one embodiment, such steps of administration or release according to the present invention is simultaneous, sequential or separate.

An individual in need as referred to herein, is in one embodiment an individual that benefits from the administration of a peptide or pharmaceutical composition according to the present invention. Such an individual in one embodiment suffers from a malignant neoplasm (tumour) in the tissue of one or more organs. In preferred examples the tumour(s) overexpresses Ran. In one embodiment the cancer is selected from cancers of the breast, lung, ovary or kidney. In one embodiment the cancer is one in which the PI3K/Akt/mTORC1 and/or Ras/MEK/ERK pathways are activated. In one embodiment the cancer is triple negative breast cancer.

The individual is in one embodiment any human being, male or female, infant, middle-aged or old.

The terms "treatment" and "treating" as used herein refer to the management and care of a patient for the purpose of combating a condition, disease or disorder. The term is intended to include the full spectrum of treatments for a given condition from which the patient is suffering, such as administration of the peptide or composition for the purpose of: alleviating or relieving symptoms or complications; delaying the progression of the condition, partially arresting the clinical manifestations, disease or disorder; curing or eliminating the condition, disease or disorder; and/or preventing or reducing the risk of acquiring the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The patient to be treated is preferably a mammal, in particular a human being. Treatment of animals, such as mice, rats, dogs, cats, cows, horses, sheep and pigs, is, however, also within the scope of the present invention. The patients to be treated according to the present invention can be of various ages, for example, adults, children, children under 16, children age 6-16, children age 2-16, children age 2 months to 6 years or children age 2 months to 5 years.

The peptides referred to are the RanGDP-RCC1 inhibitors according to the present invention and described in detail herein above.

The invention is thus, in one embodiment, directed to a peptide according to the present invention for use in the treatment of cancer in the tissue of one or more organs of a mammal. In one embodiment said treatment is ameliorative and/or curative. In one embodiment, said mammal is a human (*Homo sapiens*).

When referring to the tissue of one or more organs, said organ is in one embodiment selected from the group consisting of breast, lung, ovarian, prostate, blood, brain and renal cancers Formulation of the Peptide Inhibitors of the Invention There are a number of strategies for the delivery of peptides that may be adapted by the person of skill in the art to optimise the delivery of the peptide inhibitors of the Ran-GDP-RCC1 interaction according to the present invention. Traditionally the most common method for peptide drug delivery has been injection but this is not always suitable because, apart from potential problems associated with rapid systematic clearance, it is far from certain that the peptide can be delivered in sufficient concentration to the site of action. For certain tumours, such as those found in the prostate the peptide inhibitors of the invention can be administered directly to the site of action, i.e. the organ. Even then it is known that effective peptide transport across the cell membrane has to be achieved. It is therefore necessary to provide a formulation in which the peptide can reach its intended site of action. As a result, when considering formulation of the peptide inhibitors of RanGDP-RCC1 according to the present invention a number of factors such as potential problems with poor cellular distribution, lack of selective delivery and multidrug resistance need to be born in mind. As a consequence, it is highly desirable to provide a delivery strategy for potential peptide drugs so that they can be delivered to their site of action, i.e. to cancer cells.

One established strategy to peptide delivery involves of encapsulating the peptide drug in a suitable particulate carrier system, thereby allowing the in vivo fate of the peptide drug to be determined by the properties of the carrier system rather than its own physicochemical and transport properties. As a result, an increased therapeutic index can be achieved through control of the rate and site of drug release. Formulation options for the peptide inhibitors of the present invention thus include the use of particulate carrier systems such as liposomes, microspheres, micelles and nanoparticles.

The use of biodegradable polyester matrices, of various forms, features in many innovative approaches evaluated over the past four decades. For example, goserelin acetate peptide incorporated into PLGA copolymer, and used for treating of advanced prostate and breast cancers, was approved by the FDA in 1998. This delivery system can protect and release the peptide slowly into the systemic circulation, where it can reach its target site. In the same year, the FDA approved another two peptide drugs incorporated within polymeric carriers, the first being a poly(lactic-co-glycolic acid) (PLGA) microsphere formulation of leuprolide acetate indicated for the treatment of advanced prostate and breast cancers, and the second being a controlled release formulation based on octreotide acetate-loaded PLGA for tumour treatment in neuroendocrine disorders and carcinoid syndrome A PLGA-based microparticle formulation of triptorelin pamoate used for advanced prostate cancer and other indications, was given regulatory approval in 2000. It is envisaged that such approaches may well be suitable for the delivery of the new inhibitory peptides according to the invention.

Liposomes and colloidal nanoparticles have been used to encapsulate biologically active drugs, such as peptides, proteins and DNA in the past, with penetration through the cell membrane and intracellular delivery being demonstrated. Polymeric nanoparticles (NP) offer several advantages and those made from poly(lactic-co-glycolic acid) (PLGA) are especially beneficial. Accordingly, in one embodiment the invention relates to poly(lactic-co-glycolic acid) (PLGA) comprising nanoparticle formulation of the inhibitors of the invention. In one embodiment PLGA comprising nanoparticle formulations of the inhibitors of the invention are based on PLGA/polyethylene (PEG) block copolymer nanoparticle. In one embodiment the PEG content of the PLGA/PEG block copolymer nanoparticle is from 1% to 15%. In one embodiment the % PEG content of the PLGA/PEG block copolymer nanoparticle is from 2.5% to 10%. In one embodiment the % PEG content of the PLGA/PEG block copolymer nanoparticle is between 5% to 10%. Increasing the PEG content advantageously improves the encapsulation efficiency. It is believed that the effect of PEG is to provide a relatively hydrophilic environment in which the peptide can easily reside. The in vitro release of peptide from PLGA/PEG nanoparticles is also advantageously faster and higher than that for PLGA nanoparticles. This may well correlate with a faster and fuller release of inhibitor to the site of action in vivo.

The nanoparticle formulations of the invention are generally fabricated using emulsion solvent evaporation or by solvent displacement techniques. In one embodiment the emulsion solvent evaporation technique is used to form nanoparticle formulations of the RanGDP-RCC1 inhibitors of the invention. The nanoparticle formulations of the invention advantageously enhance the biophysicochemical properties and achieve controlled cytotoxic and apoptotic efficacy on cancer cells relative to free peptide inhibitors. The nanoparticle formulations according to the invention have a mean diameter 100 nm to 400 nm. In one embodiment the nanoparticle formulations according to the invention have a mean diameter between 150 and 300 nm. In one embodiment the nanoparticle formulations according to the invention have a zeta potential of from −3 to −10 mV. In one embodiment the nanoparticle formulations of the invention have a mean polydispersity index of between 0.3 and 0.4. Advantageously, localisation of peptide nanoparticles of the invention in the cytoplasm, where RanGDP is localised, can mediate the interaction between the blockade peptide and RanGDP thus increasing the efficacy of the dosed inhibitor through colocation of inhibitor and target.

In one embodiment the invention provides a nanoparticle formulation of a RanGDP-RCC1 inhibitor. In one embodiment the invention provides a nanoparticle formulation of a peptide RanGDP-RCC1 inhibitor according to the present invention or made according to a method of the invention.

Second Active Ingredients

In some embodiments, the peptides of the present invention are combined with or comprise one or more second active ingredients which are understood as other therapeutic compounds or pharmaceutically acceptable derivatives thereof.

Methods for treatment according to the present invention in one embodiment thus further comprise one or more steps of administration of one or more second active ingredients, either concomitantly or sequentially, and in any suitable ratios. In one embodiment, such second active ingredients is, for example, selected from compounds used to treat or prevent cancer in the tissue of one or more organs or symptoms and complications associated with treatment of cancer in the tissue of one or more organs. In one embodiment, such a second active ingredients is intended for the treatment of the side effects associated with the primary treatment or is aimed at overcoming or suppressing resistance that may arise in the cancer. Thus the one or more second active ingredients may be directed to the treatment of cancer, the treatment or suppression of emesis, the blockage of drug efflux pumps or potentiation of the anti-cancer effect of the peptide inhibitors of the Ran GDP-RCC1 interaction.

Methods of treatment according to the present invention in one embodiment include a step wherein the pharmaceutical composition or peptide as defined herein is administered simultaneously, sequentially or separately in combination with one or more second active ingredients. In preferred embodiments the action of the second therapeutic agent and the RanGDP-RCC1 inhibitors is synergistic.

Kit of Parts

In one embodiment the present invention provides a kit of parts. A kit of parts according to the present invention in one embodiment comprises one or more of the peptides or compositions as defined herein for treatment of cancer in the tissue of one or more organs. Kits according to the present invention in one embodiment allows for simultaneous, sequential or separate administration of peptides or second active ingredients as described herein.

In one embodiment of the present invention, the kit of parts comprises one or more second active ingredients as described herein.

Administration and Dosage

According to the present invention, a composition comprising a peptide inhibitor of the RanGDP-RCC1 interaction as defined herein is in one embodiment administered to individuals in need of treatment in pharmaceutically effective doses or a therapeutically effective amount.

A therapeutically effective amount of a peptide according to the present invention is in one embodiment an amount sufficient to cure, prevent, reduce the risk of, alleviate or partially arrest the clinical manifestations of a given disease or disorder and its complications. The amount that is effective for a particular therapeutic purpose will depend on the severity and the sort of the disorder as well as on the weight and general state of the subject. An amount adequate to accomplish this is defined as a "therapeutically effective amount".

In one embodiment of the present invention, the composition is administered in doses of from 1 mg/day to 5000 mg/day; such as from 1 mg/day to 100 mg/day, such as 10 mg/day to 50 mg/day, such as 100 mg/day to 250 mg/day, such as 250 mg/day to 500 mg/day, such as 500 mg/day to 750 mg/day, such as 750 mg/day to 1000 mg/day, such as 1000 mg/day to 2000 mg/day, such as 2000 mg/day to 2500 mg/day, or such as 2500 mg/day to 5000 mg/day. The dose range of active inhibitor is generally in the range of 1 to 100 mg/kg body weight, such as from 1 to 50 mg/kg body weight and more specifically 20 mg/kg body weight.

In one embodiment, a dose according to the present invention is administered one or several times per day, such as from 1 to 6 times per day, such as from 1 to 5 times per day, such as from 1 to 4 times per day, such as from 1 to 3 times per day, such as from 1 to 2 times per day, such as from 2 to 4 times per day, such as from 2 to 3 times per day. In one embodiment, the composition comprising a peptide according to the invention is administered preoperatively (before operation or surgery) and/or peroperatively (during operation or surgery).

Routes of Administration

It will be appreciated that the preferred route of administration will depend on the general condition and age of the subject to be treated, the nature of the condition to be treated, the location of the tissue to be treated in the body and the formulation of the active ingredient chosen.

In one embodiment of the present invention, the route of administration allows for the peptide to cross the blood-brain barrier.

Systemic Treatment

In one embodiment, the route of administration allows for introducing the peptide into the blood stream to ultimately target the desired site(s) of action.

In one embodiment the routes of administration is any suitable route, such as an enteral route (including the oral, rectal, nasal, pulmonary, buccal, sublingual, transdermal, intracisternal and intraperitoneal administration), and/or a parenteral route (including subcutaneous, intramuscular, intrathecal, intravenous and intradermal administration).

Appropriate dosage forms for such administration may be prepared by conventional techniques.

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration or subcutaneous administration. Furthermore, parenteral administration includes inhalations and topical administration.

Accordingly, the peptide or composition is in one embodiment administered topically to cross any mucosal membrane of an animal to which the substance or peptide is to be given, e.g. in the nose, vagina, eye, mouth, genital tract, lungs, gastrointestinal tract, or rectum, for example the mucosa of the nose, or mouth, and accordingly, parenteral administration may also include buccal, sublingual, nasal, rectal, vaginal and intraperitoneal administration as well as pulmonal and bronchial administration by inhalation or installation. In some embodiments, the peptide is administered topically to cross the skin.

In one embodiment, the intravenous, subcutaneous and intramuscular forms of parenteral administration are employed.

In one embodiment, the peptide or composition according to the invention is used as a local treatment, i.e. is introduced directly to the site(s) of action. Accordingly, the peptide may be applied to the skin or mucosa directly, or the peptide may be injected into the site of action, for example into the diseased tissue or to an end artery leading directly to the diseased tissue.

Alternative Pharmaceutical Formulations

In one embodiment, the peptides according to the present invention or pharmaceutically acceptable derivatives thereof are administered alone or in combination with pharmaceutically acceptable carriers or excipients, in either single or multiple doses. The pharmaceutical compositions or compounds according to the invention may be formulated with pharmaceutically acceptable carriers or diluents as well as any other known adjuvants and excipients in accordance with conventional techniques such as those disclosed in Remington: The Science and Practice of Pharmacy, 20th Edition, Gennaro, Ed., Mack Publishing Co., Easton, PA, 2000.

The term "pharmaceutically acceptable derivative" in present context includes pharmaceutically acceptable salts, which indicate a salt which is not harmful to the patient. Such salts include pharmaceutically acceptable basic or acid addition salts as well as pharmaceutically acceptable metal salts, ammonium salts and alkylated ammonium salts. A pharmaceutically acceptable derivative further includes esters and prodrugs, or other precursors of a compound which may be biologically metabolized into the active compound, or crystal forms of a compound.

The pharmaceutical composition or pharmaceutically acceptable composition may be specifically formulated for administration by any suitable route, such as an enteral route, the oral, rectal, nasal, pulmonary, buccal, sublingual, transdermal, intracisternal, intraperitoneal, and parenteral (including subcutaneous, intramuscular, intrathecal, intravenous and intradermal) route.

In an embodiment of the present invention, the pharmaceutical compositions or compounds of the present invention are formulated for crossing the blood-brain-barrier.

Pharmaceutical compositions for oral administration include solid dosage forms such as hard or soft capsules, tablets, troches, dragees, pills, lozenges, powders and granules. Where appropriate, they can be prepared with coatings such as enteric coatings, or they can be formulated so as to provide controlled release of the active ingredient, such as sustained or prolonged release, according to methods well known in the art. In the same solid dosage form two active ingredients may be combined so as to provide controlled release of one active ingredient and immediate release of another active ingredient.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions, as well as sterile powders to be reconstituted in sterile injectable solutions or dispersions prior to use. Depot injectable formulations are also regarded as being within the scope of the present invention.

Other suitable administration forms include suppositories, sprays, ointments, creams/lotions, gels, inhalants, dermal patches, implants, etc.

In one embodiment, a compound or peptide for use according to the present invention is generally utilized as the free substance or as a pharmaceutically derivative such as a pharmaceutically acceptable ester or such as a salt thereof. Examples of the latter are: an acid addition salt of a compound having a free base functionality, and a base addition salt of a compound having a free acid functionality. The term "pharmaceutically acceptable salt" refers to a nontoxic salt of a compound for use according to the present invention, which salts are generally prepared by reacting a free base with a suitable organic or inorganic acid, or by reacting an acid with a suitable organic or inorganic base. When a compound for use according to the present invention contains a free base functionality, such salts are prepared in a conventional manner by treating a solution or suspension of the compound with a chemical equivalent of a pharmaceutically acceptable acid. When a compound for use according to the present invention contains a free acid functionality, such salts are prepared in a conventional manner by treating a solution or suspension of the compound with a chemical equivalent of a pharmaceutically acceptable base. Physiologically acceptable salts of a compound with a hydroxy group include the anionic form of the compound in combination with a suitable cation, such as sodium or ammonium ion. Other salts which are not pharmaceutically acceptable may be useful in the preparation of compounds of the invention, and these form a further aspect of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

In one embodiment of the present invention, the peptides of the present invention are on crystalline forms, for example co-crystallized forms or hydrates of crystalline forms.

The term "prodrug" refers to peptides that are rapidly transformed in vivo to yield the parent compound of the above formulae, for example, by hydrolysis in blood or by metabolism in cells, such as for example the cells of the basal ganglia. A thorough discussion is provided in T. Higuchi and V Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference. Examples of prodrugs include pharmaceutically acceptable, non-toxic esters of the compounds of the present invention. Esters of the compounds of the present invention may be prepared according to conventional methods "March's Advanced Organic Chemistry, 5th Edition". M. B. Smith & J. March, John Wiley & Sons, 2001.

In one embodiment, for parenteral administration, solutions of peptides for use according to the present invention in sterile aqueous solution, in aqueous propylene glycol or in sesame or peanut oil are employed. Aqueous solutions should be suitably buffered where appropriate, and the liquid diluent rendered isotonic with, e.g., sufficient saline or glucose. Aqueous solutions are particularly suitable for intravenous, intramuscular, subcutaneous and intraperitoneal administration. The sterile aqueous media to be employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Moreover, the carrier or diluent may include any sustained release material known in the art, such as glyceryl monostearate or glyceryl distearate, alone or mixed with a wax. The pharmaceutical compositions formed by combining the compounds for use according to the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units, such as capsules or tablets, which each contain a predetermined amount of the active ingredient, and which may include a suitable excipient.

Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents and preserving agents in order to provide pharmaceutically elegant and palatable preparations. Tablets may contain the active ingredient(s) in admixture with non-toxic pharmaceutically acceptable excipients which are suitable for the manufacture of tablets. These excipients may, for example, be: inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, the contents of which are incorporated herein by reference, to form osmotic therapeutic tablets for controlled release.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising peptides for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the compound with a suitable non-irritating excipient which is solid at ordinary temperatures but liquid at the rectal temperature and will thus melt in the rectum to release the drug. Such materials include, for example, cocoa butter and polyethylene glycols.

Peptides of the present invention may also be administered in the form of liposome delivery systems, such as small unilamellar vesicles, large unilamellar vesicles, and multi-lamellar vesicles. Liposomes may be formed from a variety of phospholipids, such as but not limited to cholesterol, stearylamine or phosphatidylcholines.

In addition, some peptides of the present invention may form solvates with water or common organic solvents. Such solvates are also encompassed within the scope of the invention.

Thus, a further embodiment provides a pharmaceutical composition comprising a peptide for use according to the present invention, or a pharmaceutically acceptable salt, solvate, or prodrug thereof, and one or more pharmaceutically acceptable carriers, excipients, or diluents.

EXAMPLES

The present invention is illustrated by the following examples, which are not intended to limit the scope of the invention.

Materials

PLGA with a 50:50 lactic:glycolic ratio (Resomer® RG 503H, MW 34 kDa) and two PLGA-co-PEG block copolymers (Resomer® RGP d 5055 (5% PEG of MW 5 kDa) and Resomer® RGP d 50105 (10% PEG of 5 kDa molecular weight)) were purchased from Boehringer Ingelheim (Ingelheim, Germany). An 11-amino acid peptide Cys-Ala-Gln-Gly-Glu-Pro-Gly-Val-Gly-Phe-Lys (SEQ ID NO: 5) was synthesised by standard method and obtained as a white lyophilised powder with a purity of 94%. Poly(vinyl alcohol) (PVA, 87-89% hydrolysed, molecular weight 31000-50000) and phosphate buffered saline (PBS) were obtained from Sigma Chemical Co. (St. Louis, USA). A modified Lowry Protein Assay kit was obtained from Pierce Ltd. (Rockford, IL). Dichloromethane, acetonitrile and tri-flouroacetic acid were of HPLC grade and other reagents were of analytical grade. Water used in the work was produced to Type 1 standard (Milli-Q®, 18.2 MΩ cm at 25° C.).

MDA-MB-231 breast cancer cells were grown in Dulbecco's Modified Eagle Medium (DMEM) supplemented with 10% (v/v) fetal bovine serum (FBS), 2 mmol l−1 L-glutamine, 100 U ml−1 of penicillin and 100 μg ml−1 streptomycin (Invitrogen, Carlsbad, CA, USA) at 37° C. in humidified 95% air and 5% $CO_2$ with medium changed after each three-day interval.

Preparation of Peptide Loaded Nanoparticles (NP)

A modified, double emulsion, solvent evaporation method [Int J Pharmaceutics, 499 (2016) 236-246] was employed in this study. Anti-Ran-GTPase blockade peptide was dissolved in 0.2 ml of aqueous solvent to form the internal water phase and mixed with 2 ml of dichloromethane (DCM) containing 5% w/v of different polymers, then emulsified by using a Silverson L5T Homogeniser (Silverson Machines, UK) at 6,000 rpm for 2 minutes. The primary emulsion (w/o) was injected directly into a 1.25% w/v PVA solution under agitation and emulsification continued at 10,000 rpm for another 6 minutes to produce a double emulsion using the same conditions of homogenisation. The final emulsion was stirred by magnetic agitation overnight under vacuum to evaporate the organic solvent completely. After the nanospheres had formed, they were centrifuged at 22,000 g for 30 minutes at 4° C., washed three times with ultrapure water and 2% w/v sucrose solution, then lyophilised (Labconco, Kansas City, Missouri). The final product was stored in a desiccator at ambient temperature.

To make fluorescent peptide-loaded NP, coumarin 6 (100 mg) was added to the DCM phase, as the only change to the procedure described above. NP containing coumarin 6 were evaluated with respect to the drug-loading efficiency, particle size, polydispersity index (PDI) and zeta potential. Process variables, such as the polymer type, peptide loading, volume of external aqueous phase and composition of the internal aqueous phase peptide polymer interaction are listed in Table 1, together with the identifying code used to define each NP formulation.

NP Characterisation

Lyophilised NP samples (5.0 mg) were diluted with Milli-Q-water to a suitable concentration to give the recommended scattering intensity of 100 000 counts per second and suspended with vortex mixing for 5 minutes. The mean diameter and size distribution were analysed by photon correlation spectroscopy (PCS) at a fixed angle of 90° using a Malvern Zetasizer 5000 (Malvern Instruments, UK). All measurements were performed in triplicate.

Surface charge was quantified as zeta potential using laser Doppler anemometry (Malvern Zetasizer 5000, Malvern Instruments, UK). Lyophilised samples were diluted with 0.001 M KCI. Zeta potentials were calculated from the mean value of electrophoretic mobility by applying the Smoluchowski equation. All measurements were performed in triplicate.

NP surface morphology was studied using scanning electron microscopy (FEI Quanta 400 FEG SEM). Powder samples were mounted on to metal stubs then coated with a gold layer under vacuum before scanning.

Determination of Peptide Loading and Encapsulation Efficiency

Peptide content was determined by both direct extraction from lyophilised NP and by an indirect procedure based on determination of non-encapsulated peptide. In the direct method, the encapsulation efficiency was determined by a common solvent dissolution method using dimethylsulfoxide (DMSO). Freeze-dried NP (10 mg) were weighed accurately, dissolved in 1.0 ml DMSO and added to a solution of 0.1 N NaOH containing 0.5% SDS. After standing for 1 hour at room temperature, the suspension became transparent. The peptide concentration was measured by the Lowry method [Journal of Controlled Release, 107 (2005) 310-3193], giving the percentage loading (w/w, peptide mass per unit mass of dry NP). Comparison of the actual peptide loading with the theoretical peptide loading gave the percentage encapsulation efficiency.

The indirect method determined non-encapsulated peptide content in the supernatant using reverse phase chromatography [Journal of Controlled Release, 82 (2002) 429-440] (Phenomenex-Luna® C18-5 column mm, 5 μm) at a flow rate of 1.0 ml min$^{-1}$ with UV detection (254 nm). A mobile phase elution gradient was used, comprising two solvent mixtures (solvent A 0.1% TFA in acetonitrile; solvent B 0.1% TFA in water).

Peptide encapsulation in the NP was calculated from the difference between the initial amount of peptide added and the non-entrapped peptide remaining in the supernatant after NP fabrication. Each sample was assayed in triplicate and the average values using the two different assay method results were represented as the percentage peptide encapsulation efficiency.

In Vitro Release Studies

A sample of peptide-loaded NP (5.0 mg) was suspended in 1.0 ml PBS (pH 7.4) solution and incubated at 37° C. with agitation using a reciprocal shaking water bath (100 rpm). Samples were taken at predetermined time intervals of 1, 12, 24, 48, 72, 96, 120, 144 and 168 hours, replaced with fresh PBS, centrifuged for 5 minutes at 22,000 g and the peptide concentration in the supernatant determined in triplicate by HPLC assay.

Assessment of Peptide Integrity

The stability of encapsulated peptide following formulation and release from polymeric NP was determined after 7 days of in vitro release. The aqueous release medium containing peptide was analysed immediately using HPLC-MS (Applied Biosystems API 4000 LC/MS/MS). The mobile phase, at a flow rate of 1.0 ml min$^{-1}$, comprised a linear gradient of solvent B (0.1% TFA in acetonitrile) in solvent A (0.1% TFA in water) over a run time of 30 minutes. About 10-20 μl of the sample was separated using a C18 reversed phase column. The XCALIBUR® software package (Thermo scientific, USA) was used for data acquisition and analysis.

Seeding of MDA-MB-231 Cells

MDA-MB-231 cells were harvested, once confluent, and the suspension centrifuged at 1200 rpm (4° C.) for 5 minutes to sediment the cells. The pellet was resuspended in complete growth medium. A cell count was performed on a sample of suspension (10 μl) using a haemocytometer.

Cellular Uptake of NP Formulations

Cellular uptake of coumarin 6-loaded NP formulations was evaluated using flow cytometry and fluorescence microscopy [J Pharm Pharmacol 64 (2012) 61-67]. For FACS analysis, coumarin 6 tagged NP (F16, 17 and F18) were suspended in Optimem® media and added to MDA-MB-231 cells for 24 hours in 6-well plates. Cells were removed by trypsinisation and resuspended in FACS buffer. Cellular uptake of NP was quantified by gating for positive couramin 6 staining in the FITC channel following control staining with coumarin 6-treated and unstained MDA-MB-231 cells. Three independent experiments with three replicates were performed for each assay.

Cellular uptake and cellular localisation of the peptide-loaded NP was evaluated qualitatively by fluorescence microscopy by analysis of five fields per well. Intracellular uptake of coumarin 6-loaded NP (F18) into MDA-MB-231 cells was detected using fluorescence imaging 24 hours after treatment (Olympus IX70). The images were captured using digital photography (Olympus DP-71, Olympus, Center Valley, PA, USA). MDA-MB-231 cells where seeded into a 6-well plate, containing two fixed cover slips and 2.0 ml of growth medium. After washing the cells with sterile PBS, the coverslips were removed, mounted with fixing media over a glass slide and examined. The untreated MDA-MB-231 cells and cells treated with a solution of coumarin 6 were used as positive and negative controls.

Cytotoxicity Studies

Cytotoxicity of an optimised peptide NP formulation (F18) containing peptide of SEQ ID NO: 5 was measured by assessing cell viability (MTT assay). The MDA-MB-231 cells were seeded in 24-well plates (Nalgen Nunc International, Ochester, NY) at a density of $5\times10^4$ cells per well and incubated for 24 hours to allow for 60-70% confluency and sufficient adhesion. The cells were treated with different concentrations of the peptide-loaded NP, free peptide (SEQ ID NO: 5) and blank NP. After 24, 48, 72 and 96 hours, the treated cells were washed with 500 µl PBS, and 500 µl of 15% MTT dye solution in complete media added to each well. The plates were incubated at 37° C. and 5% $CO_2$ for an additional 3 hours. The supernatant was then discarded, 500 µl DMSO added and the solution vigorously mixed. The optical density of each well was measured at 570 nm (reference wavelength 630 nm) in a microplate reader (Fluostar Omega, BMG Lab Tech GMBH, Germany). This experiment was performed in triplicate and repeated three times. Mean values±SD for each concentration was determined. Percentage cell viability was determined as the ratio of absorbance (570 nm) in treated cells relative to the absorbance in control cells (570 nm). The absorbance of the untreated cells was set at 100%. The $IC_{50}$ was defined as the concentration of sample needed to reduce the signal by 50% relative to the control.

Cell Cycle Analysis

To determine the effect of peptide (SEQ ID NO: 5)-loaded NP on cell growth, cultured cells were treated with the same doses of free peptide and peptide-loaded NP as used in the cell viability assay. After 24 and 48 hours of treatment, cells were suspended in PBS and fixed by addition of 70% ice-cold methanol. Cells were treated by adding RNase (1.0 µg $ml^{-1}$) to the samples and re-suspending in propidium iodide (PI) stain (5.0 µg $ml^{-1}$). PI fluorescence intensity was determined using flow cytometry through a FL-2A filter at 585 nm. Flow-cytometric data were analysed using Cyflogic (v.1.2.1) software. Quantification of apoptotic cells was determined by flow cytometry as the percentage of cells in the sub-G1 region (hypodiploidy) in cell cycle analysis as previously described [PLoS ONE, 6 (2011) e23640].

Statistical Analysis

Results are presented as mean±SD and analysed statistically using one-way analysis of variance (ANOVA) followed by Tukey's post hoc test. A value of $p<0.05$ was considered statistically significant.

TABLE 1

Process variables for peptide (SEQ ID NO: 5)-loaded NP and corresponding identifiers

| Formulation identifier | Polymer type | Peptide Loading (%) | Internal aqueous phase Solvent* | External aqueous phase volume (ml) |
|---|---|---|---|---|
| F1 | PLGA | 6 | PBS | 50 |
| F2 | PLGA | 6 | PBS | 75 |
| F3 | PLGA | 6 | PBS | 100 |
| F4 | 5% PEG-PLGA | 6 | PBS | 50 |
| F5 | 5% PEG-PLGA | 6 | PBS | 75 |
| F6 | 5% PEG-PLGA | 6 | PBS | 100 |
| F7 | 10% PEG-PLGA | 6 | PBS | 50 |
| F8 | 10% PEG-PLGA | 6 | PBS | 75 |
| F9 | 10% PEG-PLGA | 6 | PBS | 100 |
| F10 | PLGA | 4 | PBS | 100 |
| F11 | PLGA | 2 | PBS | 100 |
| F12 | 5% PEG-PLGA | 4 | PBS | 100 |
| F13 | 5% PEG-PLGA | 2 | PBS | 100 |
| F14 | 10% PEG-PLGA | 4 | PBS | 100 |
| F15 | 10% PEG-PLGA | 2 | PBS | 100 |
| F16 | PLGA | 2 | 0.1M HCl | 100 |
| F17 | 5% PEG-PLGA | 2 | 0.1M HCl | 100 |
| F18 | 10% PEG-PLGA | 2 | 0.1M HCl | 100 |

*PBS—phosphate buffered saline (pH 7.4)

TABLE 2

Effects of different process variables on peptide (SEQ ID NO: 5)-loaded NP size, PDI, zeta potential and encapsulation efficiency

| Formulation ID | Size (nm)* | PDI* | Zeta Potential (-mV)* | Encapsulation Efficiency (%)* |
|---|---|---|---|---|
| F1 | 330.0 ± 20.1 | 0.26 ± 0.04 | −18.90 ± 2.60 | 36.99 ± 2.19 |
| F2 | 355.0 ± 21.6 | 0.34 ± 0.03 | −19.15 ± 2.07 | 43.99 ± 4.47 |
| F3 | 363.5 ± 4.6 | 0.45 ± 0.03 | −20.53 ± 1.91 | 50.66 ± 4.38 |
| F4 | 250.3 ± 12.8 | 0.39 ± 0.03 | −4.91 ± 1.29 | 45.56 ± 0.78 |
| F5 | 265.3 ± 26.2 | 0.41 ± 0.02 | −5.41 ± 0.92 | 49.23 ± 2.88 |
| F6 | 325.3 ± 26.9 | 0.41 ± 0.03 | −5.43 ± 1.72 | 59.89 ± 6.89 |
| F7 | 217.3 ± 11.1 | 0.31 ± 0.02 | −5.05 ± 1.17 | 54.88 ± 2.64 |
| F8 | 225.0 ± 16.7 | 0.33 ± 0.01 | −5.55 ± 0.98 | 58.88 ± 8.62 |
| F9 | 274.8 ± 19.6 | 0.34 ± 0.02 | −6.28 ± 1.92 | 68.39 ± 2.09 |
| F10 | 327.5 ± 21.5 | 0.44 ± 0.02 | −18.90 ± 2.55 | 59.66 ± 2.36 |
| F11 | 312.5 ± 39.3 | 0.42 ± 0.03 | −19.53 ± 2.71 | 67.66 ± 6.86 |
| F12 | 247.8 ± 16.3 | 0.38 ± 0.03 | −4.91 ± 1.29 | 68.98 ± 3.28 |
| F13 | 178.5 ± 25.7 | 0.39 ± 0.03 | −5.61 ± 2.19 | 77.50 ± 3.11 |
| F14 | 210.0 ± 31.3 | 0.32 ± 0.02 | −5.05 ± 1.17 | 73.87 ± 4.16 |
| F15 | 161.8 ± 15.7 | 0.30 ± 0.03 | −6.11 ± 2.39 | 80.52 ± 6.08 |
| F16 | 276.5 ± 12.3 | 0.40 ± 0.02 | −15.65 ± 2.35 | 93.66 ± 2.59 |
| F17 | 196.0 ± 19.5 | 0.36 ± 0.05 | −3.31 ± 1.62 | 86.50 ± 2.51 |
| F18 | 181.8 ± 08.5 | 0.31 ± 0.03 | −4.51 ± 2.12 | 90.19 ± 1.76 |

*All values are mean ± SD with n = 3

Discussion of Results

Polymeric NP loaded with peptide (SEQ ID NO: 5) were fabricated by the double emulsion solvent evaporation method and physicochemical parameters, such as mean particle size, PDI, zeta potential, encapsulation efficiency and in vitro release profile determined. The impact of different formulation variables on the physicochemical characteristics of the peptide-loaded NP was investigated to optimise the formulation of peptide-loaded NP and ensure suitable NP size, high peptide loading and controlled therapeutic action.

Effect of Polymer Type

The physicochemical characterisations of different peptide-loaded NP (F1, F4 and F7) generated from three different polymers were investigated. PLGA NP (F1) (330.0±20.1 nm) were significantly larger in size ($p<0.001$) than NP prepared from PEGylated polymers of F4 (250.2±12.8 nm) and F7 (217.3±11.1 nm) for 5 and 10% PEG-PLGA diblock copolymers, respectively (FIG. 1, panel A). This was attributed to the role of covalently linked hydrophilic PEG blocks in modifying the physicochemical properties of PLGA polymer that led to formation of smaller particles. All NP formulations were of low polydispersity index ranging from 0.26 to 0.39. Increasing the PEG fraction in the NP matrix resulted in a decrease in the mean NP diameter, which is a similar finding to that reported in other studies.

The ζ-potential of NP plays an important role in stability. F1 exhibited higher negative ζ-potential values (−18.9±2.6 mV) compared to the PEGylated PLGA NP (F4 and F7) ($p<0.001$) (FIG. 1, panel B). Increasing the PEG fraction from 5% to 10% had no effect on the potential. The PEG-PLGA NP had a lower negative ζ-potential, relatively close to neutral, due to the presence of surface-located PEG chains that shield free carboxylic groups responsible for the overall negative particulate surface charge.

Increasing the PEG fraction in the polymer backbone resulted in a significant increase in peptide entrapment ($p<0.01$). Encapsulation efficiency was increased from (37.0%±2.2%) in PLGA to (54.9%±2.6%) in 10% PEG-PLGA (FIG. 1, panel C). In the diblock types, PEG chains orient themselves towards the aqueous phase in micelles, surrounding the encapsulated peptide. The diblock copolymer types facilitated high drug loading and encapsulation efficiency of the protein drug. This contribution of PEG-PLGA polymer is believed to be due to the relatively hydrophilic microenvironment created by the PEG segment, in which the encapsulated peptide can easily reside. The higher encapsulation efficiency of 10% PEG-PLGA is believed to be in part due to its lower solubility in methylene chloride that led to shorter solidification time and, consequently, higher encapsulation efficiencies.

The in vitro release profile showed that the burst release of peptide was faster and significantly higher ($p<0.001$) from PEGylated PLGA NP when compared to PLGA NP. F4 and F7 released approximately 62.6%±2.5% and 70.4%±6% of peptide within the first 24 hours compared to 51.5%±1.5% released from the F1 (FIG. 1D).

Effect of External Aqueous Phase Volume

Three different volumes of the external phase (50, 75 and 100 ml) were used to investigate the effect of this process variable on the physicochemical properties of different NP formulations of PLGA (F1, F2 and F3), 5% PEG-PLGA (F4, F5 and F6) and 10% PEG-PLGA (F7, F8 and F9). An increase of the volume of PVA solution from 50 ml to 100 ml caused an insignificant increase in size ($p>0.05$) of the PLGA NP (FIG. 2, panel A) with a significant increase ($p<0.001$) in PDI from 0.26±0.04 to 0.45±0.02. However, a slight increase in PDI with a significant increase in size from 250 nm to 325 nm and from 217 nm to 274 nm was observed for 5% and 10% PEGylated PLGA NP, respectively. Conversely, the increase in external PVA solution to 100 ml resulted in a significant increase in size ($p<0.01$) of 5% and 10% PEGylated PLGA NP from 250.3±12.8 nm to 325.5±27 nm and from 217.3±11.1 nm to 274.8±19.6 nm for 5% and 10% PEGylated PLGA NP, respectively. However, an insignificant decrease in PDI values ($p>0.05$) was observed.

Figure 2:
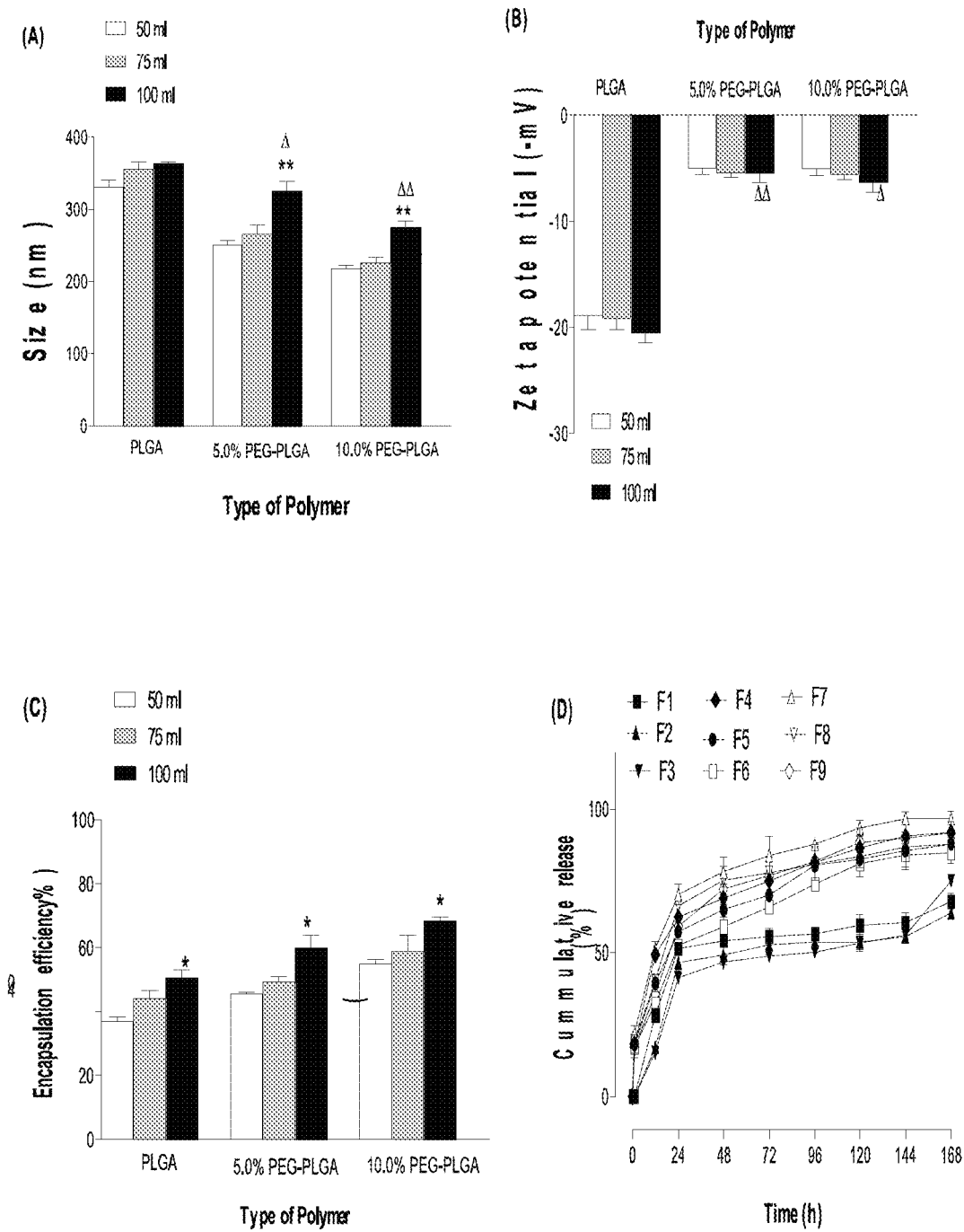
FIG. 2 illustrates the effect of the external aqueous phase volume on nanoparticles containing peptide of SEQ ID NO: 5 on (panel A) size, (panel B) zeta potential, (panel C) encapsulation efficiency and (panel D) in vitro peptide release. Values are mean±SD with n=3. For FIG. 2, panels A-C, $*p<0.05$, $p<0.01$, $*p<0.001$ compared with 50 ml for each polymer type. $\Delta p<0.05$, $\Delta\Delta p<0.01$, $\Delta\Delta\Delta p<0.001$ compared with 75 ml for each polymer type.

Preparation of peptide-loaded NP with different volumes of the external aqueous phase had no significant effect on zeta potential ($p>0.05$) (FIG. 2, panel B). Encapsulation efficiency increased as the volume of the continuous phase increased (FIG. 2, panel C). For example, when the ratio of dispersed phase to continuous phase (DP/CP) was decreased to 1/50, the encapsulation efficiency significantly increased ($p<0.05$) by a factor of 36.9% (PLGA), 31.5% (5% PEG-PLGA) and 24.6% (10% PEG-PLGA) when compared to the higher DP/CP ratio of 1/25. It was likely that a large volume of continuous phase provides nearly a sink condition for diluting the organic solvent so that DCM was extracted instantly resulting in fast solidification of the polymer that eventually led to higher entrapment for the hydrophilic peptide. In vitro release profiles showed that external phase volume influenced the initial burst release and the controlled release pattern from different polymers (FIG. 2, panel D). Higher burst release had been observed from F1, F4 and F7 with low external volume compared to F3, F6 and F9. In fact, porosity increased with increasing DP/CP ratio due to decreasing the rate of the polymer solidification. For low external volume, the solidification is slower. Water is able to influx from either the aqueous phase (external and internal) into the polymer structure, which creates water-filled channels or pores. Hence, a higher initial burst release occurs. However, polymer solidification is moderately fast for F3, F6 and F9 and water is less able to interact with the matrix, resulting in a dense structure and low initial release.

Effect of Peptide Loading

Figure 3:
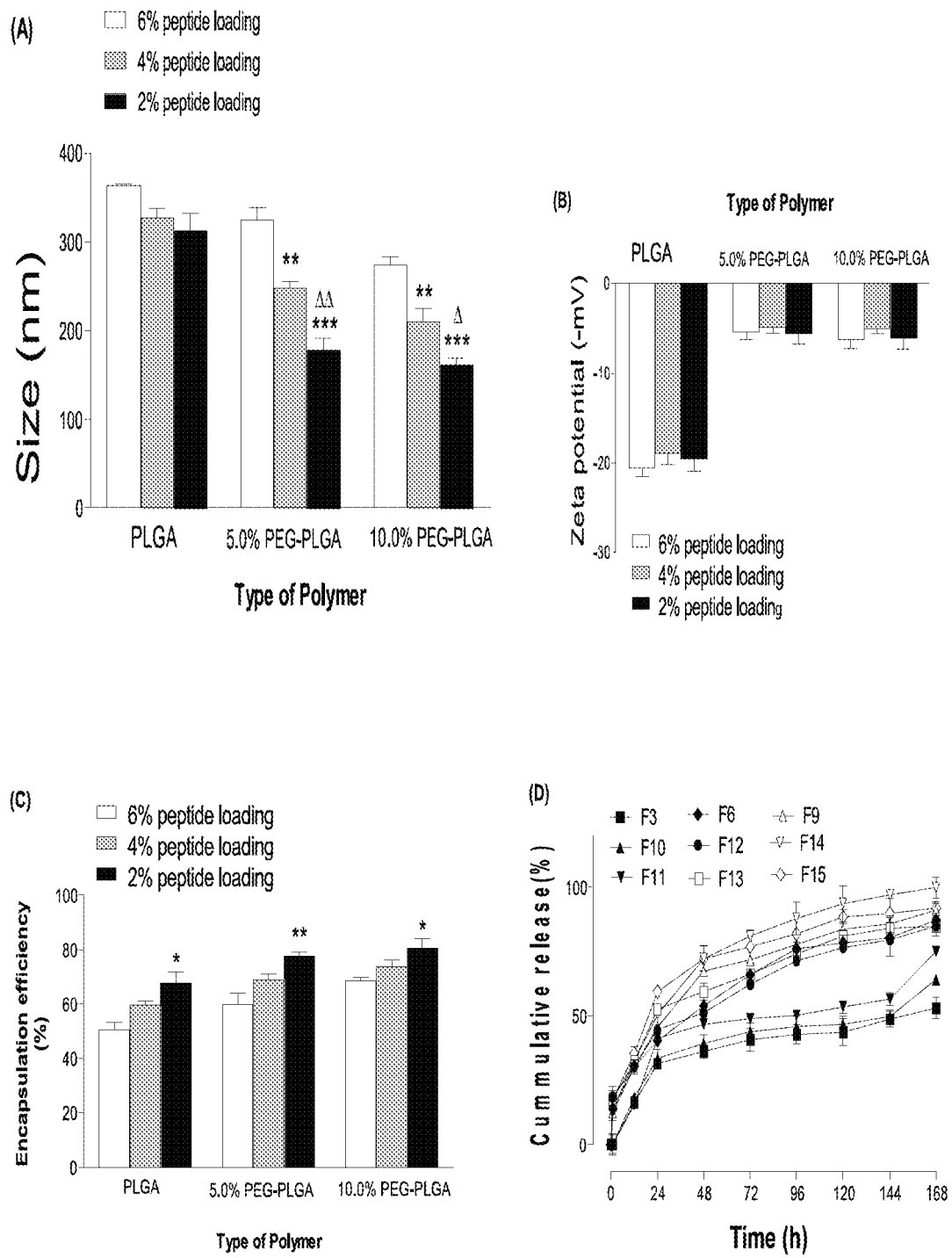
FIG. 3 illustrates the effect of peptide loading on nanoparticles containing peptide of SEQ ID NO: 5 on (panel A) size, (panel B) zeta potential, (panel C) encapsulation efficiency and (panel D) in vitro peptide release. Values are mean±SD with n=3. For FIG. 3, panels A-C, $*p<0.05$, $p<0.01$, $*p<0.001$ compared with 6% peptide loading for each polymer type. $\Delta p<0.05$, $\Delta\Delta p<0.01$, $\Delta\Delta\Delta p<0.001$ compared with 4% peptide loading for each polymer type.

Three different loadings were used in this study (6%, 4% and 2%) to investigate the effect on the physicochemical characterisation of different NP formulations of PLGA (F3, F10 and F11), 5% PEG-PLGA (F6, F12 and F13) and 10% PEG-PLGA (F9, F14 and F15). Decreasing peptide loading resulted in a non-significant decrease in the size of PLGA NP ($p>0.05$) (FIG. 3, panel A). However, decreasing the peptide loading from 6% to 2% in PEG-PLGA formulations resulted in a significant decrease in NP size ($p<0.001$). NP size decreased from 325.5±27 nm to 178.5±25.7 nm and from 274.8±19.6 nm to 161.8±15.7 nm for 5% and 10% PEGylated NP, respectively. Increasing the peptide loading increased the amount bound to the NP surface due to presence of PEG moieties, which led to an increase in the average NP diameter. PDI values reduced following a decrease in peptide loading, with no significant effect on the surface charge (FIG. 3, panel B). Peptide loading had a significant impact on the encapsulation efficiency in all types of NP. The decrease in peptide loading resulted in a significant increase in encapsulation efficiency ($p<0.05$) (FIG. 3, panel C). Encapsulation efficiencies increased from 50.7%±4.4% to 67.7%±6.9% (PLGA), from 59.9%±6.9% to 77.5%±3.1% (5% PEG-PLGA) and from 68.4%±2.1% to 80.5%±6.1% (10% PEG-PLGA).

The release profiles and the initial bursts were closely related to the degree of peptide loading (FIG. 3, panel D). The release profile of F3, F6 and F9 with a loading of 2% was significantly lower than those of 6% loading ($p<0.01$). Initial bursts of 41.4%±2.2%, 52.5%±3.2% and 59.4%±2.0% were observed from F3, F6 and F9, respectively, compared to 31.5%±1.0%, 40.3%±1.5% and 45.5%±1.5% from F11, F13 and F15, respectively. Using increased amounts of peptide in the primary emulsion droplets enhanced the concentration gradient towards the external water phase, which led to increased outward diffusion.

Effect of Drug Polymer Interaction

The influence of peptide interaction with the polymer on NP properties was investigated. Peptide was dissolved in two aqueous solvent types (PBS and 0.1 M HCl pH 1.0) to investigate the effect of possible ionic interaction on the physicochemical characterisation of different NP formulations of PLGA (F11 and F16), 5% PEG-PLGA (F13 and F17) and 10% PEG-PLGA (F15 and F18). RanGDP-RCC1 inhibitor peptide (SEQ ID NO; 5) is a neutral peptide with a MW of 1234 Da and an isoelectric point (pI) around 6.0. The peptide dissolved in PBS is unlikely to interact with the anionic PLGA polymers because of its almost neutral charge. Alternatively, in 0.1 M HCl, the peptide was dissolved at a pH that would render it cationic. Since the peptide of SEQ ID NO: 5 has a positive charge at acidic pH, it was expected that electrostatic interaction between basic amino acid residues of the peptide and the uncapped carboxylic acid terminal end group in the PLGA played a key role in the peptide encapsulation and release.

Figure 4:
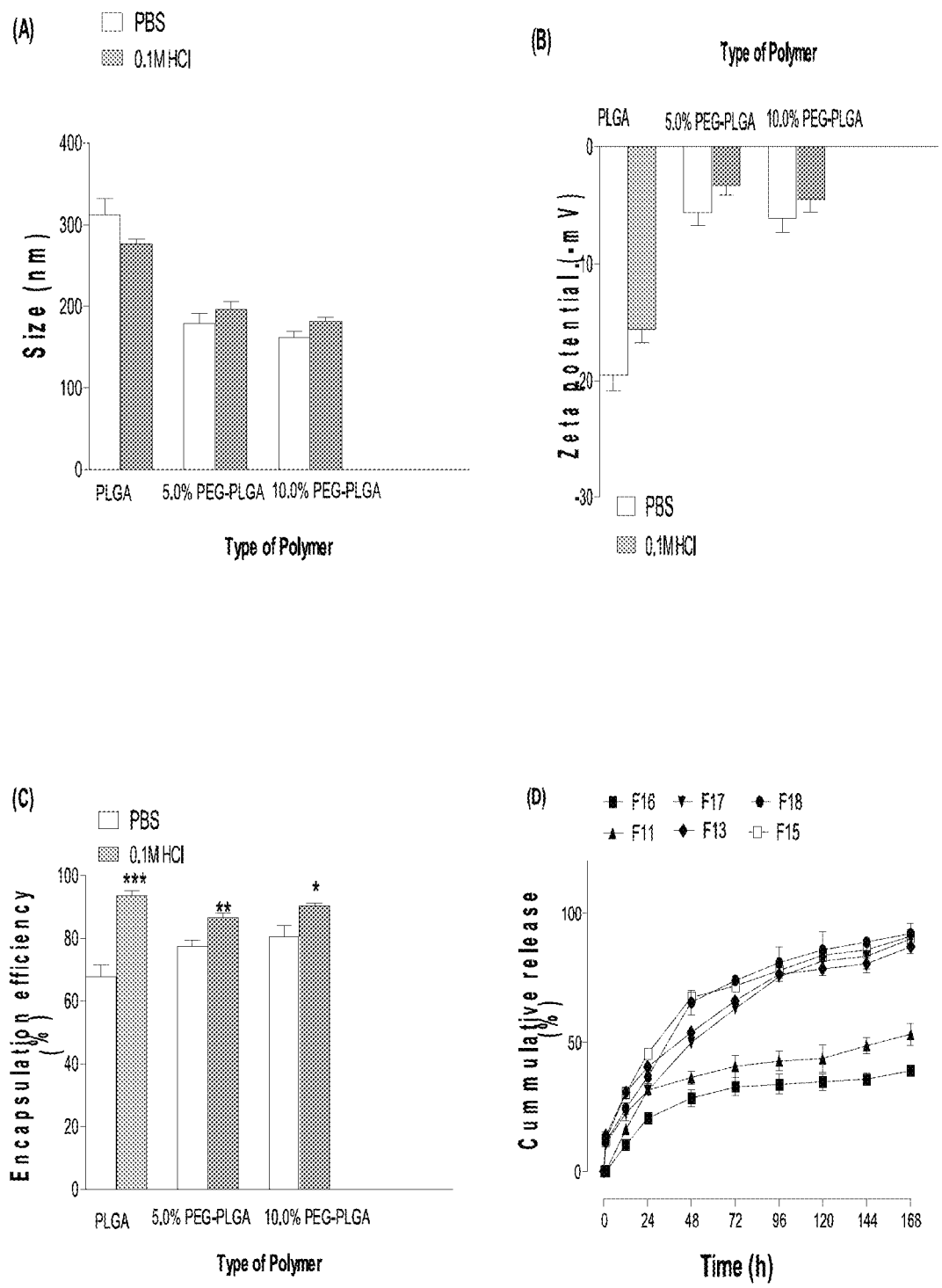
FIG. 4 illustrates the effect of peptide (SEQ ID NO: 5) polymer interaction on (panel A) nanoparticle size, (panel B) zeta potential, (panel C) encapsulation efficiency and (panel D) in vitro peptide release. Values are mean±SD with n=3. For FIG. 4, panels A-C, $*p<0.05$, $p<0.01$, $*p<0.001$ compared with PBS for each polymer type.

The predicted peptide polymer interaction had no significant impact on NP size and PDI (FIG. 4, panel A), although there was evidence that it influenced the zeta potential values of the final NP ($p>0.05$) (FIG. 4, panel B). Conversely, interaction between peptide and polymer contributed to increasing encapsulation efficiency in all polymer types. A sharp increase in peptide encapsulation efficiency was observed for the PLGA polymer ($p<0.001$), which exceeded that for the other PEGylated polymers (FIG. 4, panel C). The abundance of free carboxyl groups, which are more prevalent in PLGA when compared to the PEGylated PLGA copolymers, could explain this observation. This ionic interaction would advantageously retard peptide diffusivity to the external aqueous phase during the preparation process and impede unwanted loss. Encapsulation of cationic peptides within uncapped polymers that carry free carboxylic end groups is generally preferable to the end-capped variants.

Figure 5:
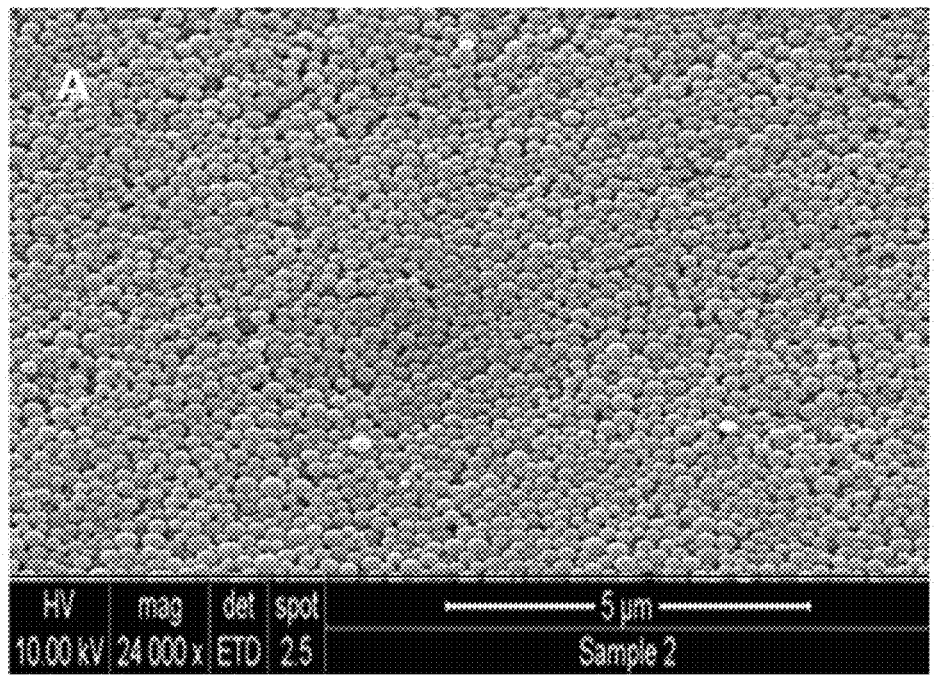
FIG. 5 presents SEM images of SEQ ID NO 5 peptide-loaded nanoparticle (F18) (panel A) after formulation and (panel B) after 7 days of in vitro release. Panel C is an electron spray mass spectrum of peptide release after 7 days.
Figure 5:
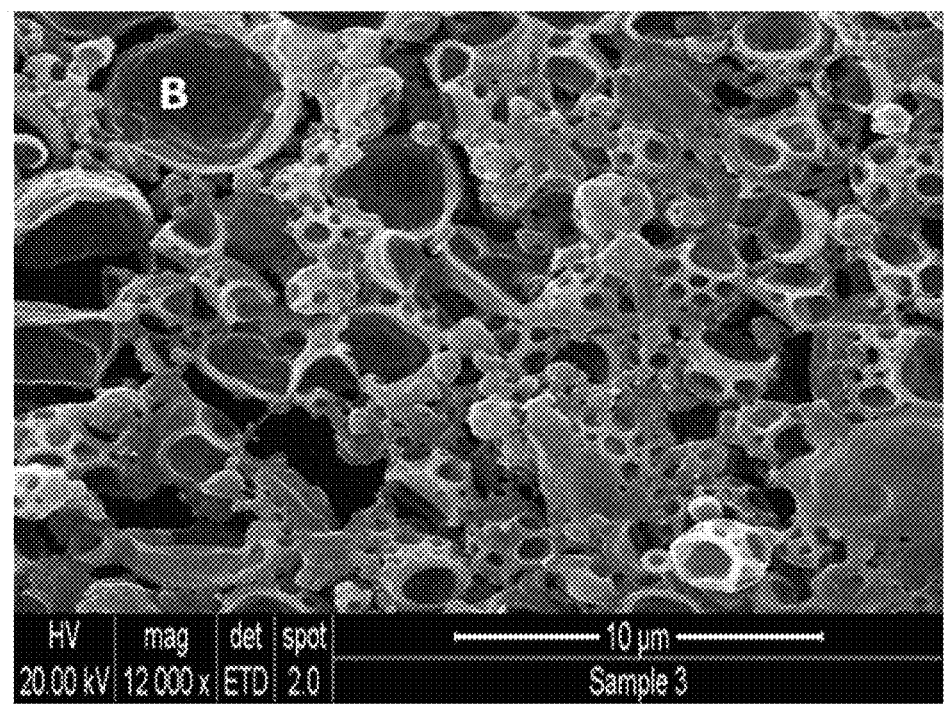

Interactions between polymer and protein are predicted to influence release from the final delivery system. In vitro release profiles of PLGA NP showed initial burst releases followed by a slower release profile during the remainder of the incubation period (FIG. 4, panel D). To confirm the ionic interaction, different amounts of NaCl were added to the release medium (data not shown), and the in vitro release profiles compared. The results showed more release at higher concentrations of NaCl. The burst release at 0.0 M NaCl was 20.1±2% which increased to 42.7±3.4% by adding 0.5 M NaCl for PLGA NP. Increases in ionic strength of the medium reduces the extent of ionic interaction by shielding charged ionic groups. These results suggest that there is an ionic interaction between the peptide and PLGA. Such an interaction could explain the slow release of the peptide from the PLGA NP. These results reveal that release of peptide from PLGA NP is not only controlled by degradation or erosion of the polymer, but also due to the possible ionic interaction. However, for PEGylated PLGA polymers, the entrapped peptide could be released when the polymer was completely degraded. Consequently, the peptide release was governed by the degradation rate of the polymer, as 90% release was achieved over 7 days. This suggests that the interaction between peptide and polymer did not influence the stability of the peptide within PEGylated PLGA NP and during its release. Stability was further assured by mass spectroscopy, which confirmed that the peptide mass was unaltered following in vitro release from F18 (FIG. 5, panel C).

Scanning Electron Microscopy

To access the surface morphology, aggregation or adhesion of peptide-loaded NP (F18), SEM was used to visualize the particulate surface. SEM images revealed a smooth spherical shape of homogenous size, with no evidence of particle adhesion or aggregation (FIG. 5, panel A). The average size obtained from SEM was comparable to what obtained by laser diffraction. After 7 days of in vitro release, exhausted NP samples appeared to have a more porous and labyrinthine structure. This structure would result from drug diffusion after the erosion of the polymer by the aqueous release media (FIG. 5, panel B).

Cellular Uptake of Nanoparticles

Figure 6:
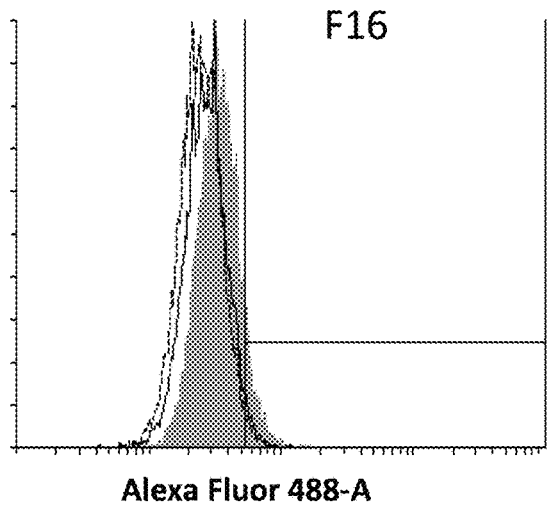
FIG. 6 shows the quantitative cellular uptake of different types of SEQ ID NO: 5 peptide nanoparticles after 24 hours, as determined by flow cytometry. The individual histograms represent the percentage positive cellular uptake of (panel A) F16, (panel B) F17 and (panel C) F18 nanoparticles (see Tables 1 and 2 for information on these formulations) and (panel D) a direct comparison of cellular uptake of each of nanoparticles F16, F17 and F18. Values are mean±SD with n=3. $***p<0.001$ compared with all other treatments.
Figure 6:
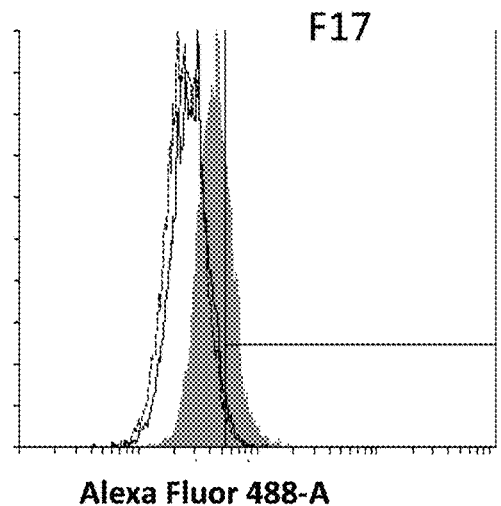
Figure 6:
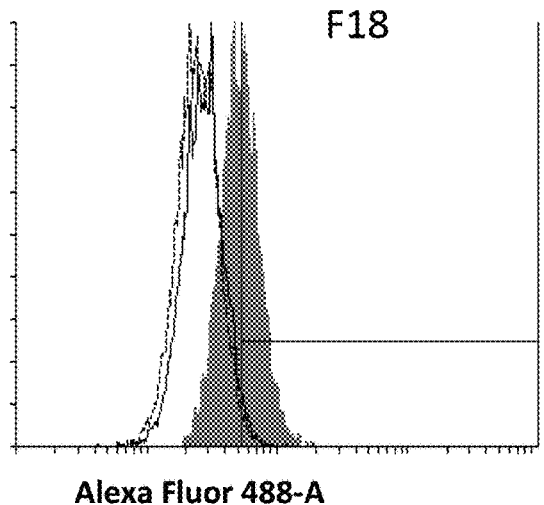
Figure 6:
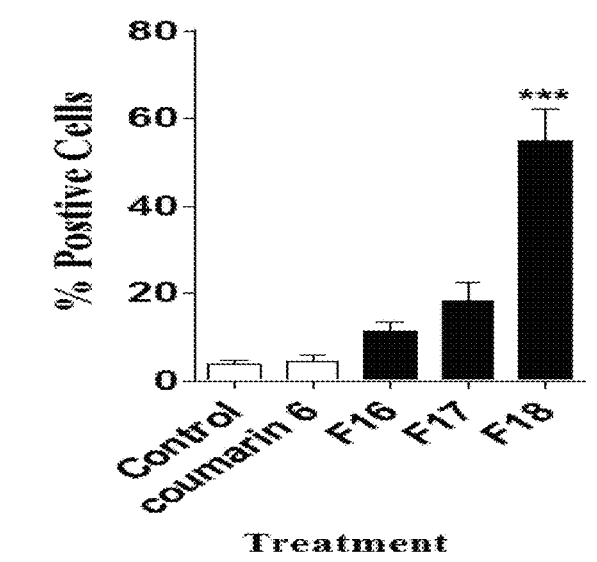
Figure 7:
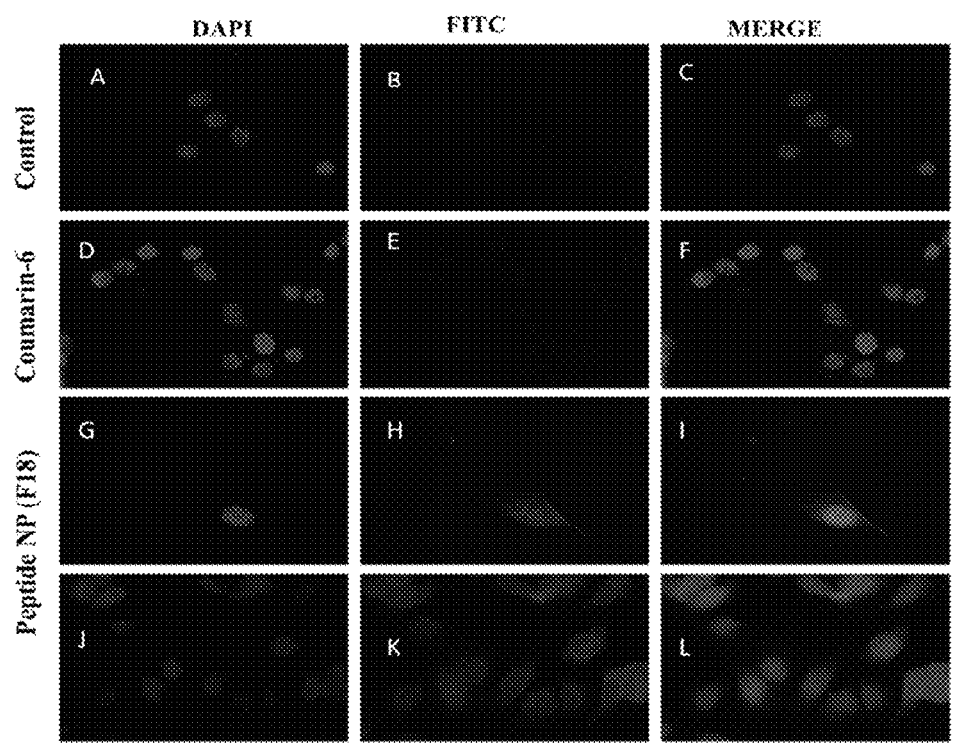
FIG. 7 presents fluorescence microscope images of control cells (panels A-C), cells treated with coumarin 6 (panels D-F) and coumarin 6+peptide of SEQ ID NO: 5-loaded nanoparticles (F18) (panels G-L) after 24 hours of treatment stained with DAPI (first column), FITC (second column) and a merge of columns 1 and 2 (third column).

The efficiency of cellular uptake of PLGA and PEGylated PLGA NP by MDA-MB231 breast cancer cells was investigated. Results of in vitro cellular uptake studies are shown in FIGS. 6 and 7. The quantitative flow cytometry analysis, which reflected the presence of the coumarin 6 loaded, peptide NP in breast cancer cells after 24 hours of treatment is shown in FIG. 6, panels A-D. The percentage of cells with positive staining following treatment with 10% PEGylated NP was significantly higher (p<0.001) than all other NP formulations made from PLGA and 5% PEG-PLGA. F18 showed higher cellular uptake with 54.8%±12.7% positive cells, compared to 11.4%±3.7% and 18.1%±7.3% with F16 and F17, respectively. These results showed that F18, with the lowest particle size (162 nm), highest PEG content and lowest zeta potential (−4.5 mV) gave rise to the greatest uptake by MDA-MB-231 cells.

PEGylated PLGA NP showed significantly higher cellular uptake when compared to PLGA NP, due to PEGylation, especially for the 10% PEG-PLGA copolymer type. This suggests that particle size is a key determinant of cellular uptake. Fluorescence microscopy studies confirmed that F18 exhibited the largest uptake in MDA-MB-231 cells (FIG. 7). The peptide NP were primarily localised in the cytoplasmic compartment, while some fluorescence intensity was observed in the perinuclear region (FIG. 7, panels G-L). The coumarin 6 solution uptake by cells showed minimal internalisation (FIG. 7, panels D-F). Based on these quantitative and qualitative results, of the nanoparticle systems assessed 10% PEGylated PLGA NP showed maximum cellular uptake. Moreover, localisation of peptide nanoparticle in the cytoplasm, where RanGDP is localised, can mediate the interaction between the blockade peptide and RanGDP. Due to these observations, F18 was selected for further studies due to its enhanced cellular uptake in the test cancer cells.

In Vitro Cytotoxicity

Figure 8:
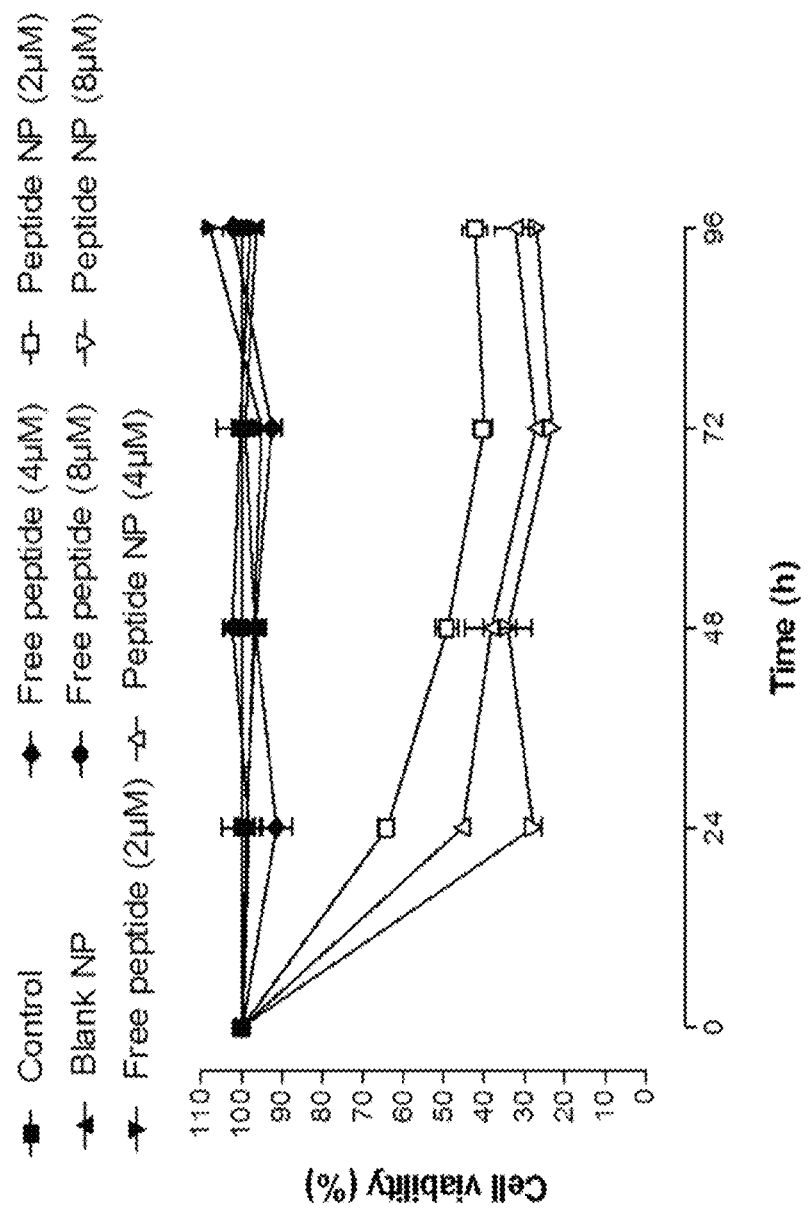
FIG. 8 shows MDA-MB-231 cell viability results of different doses of free peptide of SEQ ID NO: 5 and peptide of SEQ ID NO: 5 nanoparticle F18 (labelled Peptide NP) after 24, 48, 72 and 96 hours.
Figure 9:
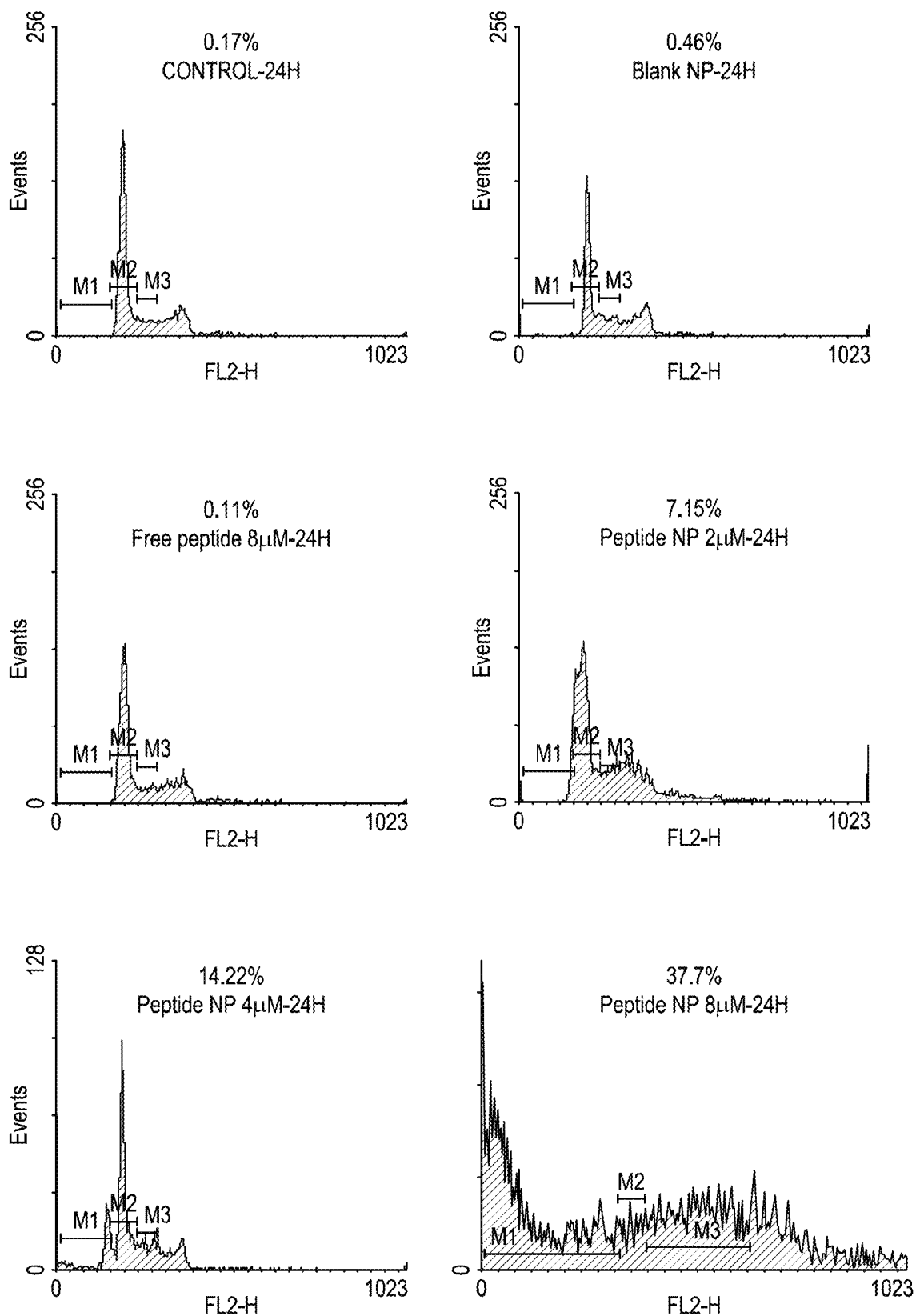
FIG. 9 shows MDA-MB-231 cell cycle analysis results of different doses of free peptide of SEQ ID NO: 5 and peptide of SEQ ID NO: 5 nanoparticle F18 (labelled Peptide NP) after 24 and 48 hours.

The cytotoxic action of peptide-loaded NP on the MDA-MB-231 cell line was evaluated by MTT assay after 24, 48, 72 and 96 hours of treatment at 2, 4 and 8 µM of free peptide and peptide-loaded NP (F18). The dose effect curves were generated to detect the drug concentration that caused 50% growth inhibition (IC50). The results indicate that the blank NP and, at the concentrations evaluated in this study, the free peptide had no significant cytotoxicity on breast cancer cells (FIG. 8). The lack of significant cytotoxicity for the free peptide probably reflects that only a small amount of free peptide reaches the cytoplasm due to inefficient transport of this particular peptide across the cell membrane. Peptide-loaded NP reduced cell viability and a sustained cytotoxic action was achieved for up to four days after treatment. The mean IC50 value for peptide-loaded 10% PEG-PLGA NP in MDA-MB-231 cells was 3.6 µM, which was achieved within 24 hours. The nanoparticle (NP) can deliver peptide to its subcellular site, protect it from degradation and enable interaction with RCC1 and thus inhibit the RanGDP-RCC1. Peptide-loaded nanoparticles (NP) achieved lower cell viability and greater cytotoxicity when compared to the free peptide after 24, 48, 72 and 96 hours of treatment.

Cell Cycle Analysis

The results of cell cycle analysis of MDA-MB-231 cells revealed that cancer cells treated with peptide-loaded nanoparticles (NP) were arrested at the mitotic division stage of the G0/G1 and G2/M phase. Peptide-loaded nanoparticles (NP) showed a stronger effect after 48 hours. Peptide-loaded NP at concentrations of 4 and 8 µM caused significantly higher G0/G1 phase arrest of 31.2% and 55.4% after 48 hours, compared to results after 24 hours of 14.2% and 37.7%, respectively, using similar concentrations. Concomitantly, the growth rate of the cells was also reduced after peptide-loaded NP treatment, whereas cells treated with free peptide were not affected. This confirms the peptide blockade effect on Ran by inhibition of RanGTP formation and its role in cell mitosis.

Ran Activation Assay

Results of a RAN activation assay are provided in FIG. 14. In this figure, Lane 1 is positive control (activated Ran protein); Lane 2, MDA MB-231 cell lysate; Lane 3 MDA MB-231 cell lysate loaded with GDP and incubated (negative control) with RanBP1 Agarose beads; Lane 4, MDA MB-231 cell lysate loaded with GTPγS (positive control) incubated with RanBP1 Agarose beads; Lane 5, MDA MB-231 cell lysate treated by peptide of SEQ ID 5; Lane 6, MDA MB-231 cell lysate loaded with GD and treated with peptide of SEQ ID 5; and Lane 7, MDA MB-231 cell lysate loaded with GTPγS and treated with peptide of SEQ ID 5 incubated with RanBP1 Agarose beads.

This experiment demonstrates that the peptide inhibitor of SEQ ID 5 disturbs the interaction between Ran-GDP and RCC1 (compare Lane 2 with Lane 5) in native cells. It also shows that peptide inhibitor of SEQ ID 5 disturbs the interaction between RanGDP-RCC1 away from the GTP binding pocket (compare Lanes 4 & 7). From these results it can be concluded that peptide inhibitor of SEQ ID 5 disrupts the normal interaction between Ran-RCC1 by binding to RCC1 in the region that normally binds in RanGDP in the formation or stabilisation of the RanGDP-RCC1 complex.

The invention claimed is:

1. A method for inhibiting the binding of regulator chromosome condensation 1 (RCC1) to GDP bound Ras-related nuclear proteins (RanGDP) in a subject in need thereof, wherein one or more cells of the subject overexpress Ras-related nuclear protein (RAN), comprising administering to the subject a therapeutically effective amount of a peptide comprising the amino acid sequence of SEQ ID NO:5 to inhibit the binding of RCC1 to RanGDP in the one or more cells overexpressing RAN.

2. The method of claim 1, wherein the therapeutically effective amount is administered by direct administration as a medicine.

3. The method of claim 1 wherein the peptide comprising the amino acid sequence of SEQ ID NO:5 is further transformed into an alternative pharmaceutically acceptable form.

4. The method of claim 3 wherein the alternative pharmaceutically acceptable form is a nanoparticle.

5. The method of claim 3 wherein the alternative pharmaceutically acceptable form is an antibody.

6. The method of claim 3 wherein the alternative pharmaceutically acceptable form is an antibody-drug conjugate.

7. The method of claim 1 wherein an administered dose is from 1 mg/day to 5000 mg/day.

8. The method of claim 1 wherein a dose range is 1 to 100 mg/kg body weight.

9. The method of claim 1 wherein the composition is administered from 1 to 6 times per day.

10. The method of claim 1 wherein the composition is administered directly to a tumour site.

11. The method of claim 1, wherein the peptide comprising the amino acid sequence of SEQ ID NO:5 is in a nanoparticle formulation.

12. The method of claim 11, wherein the nanoparticle comprises poly(lactic-co-glycolic acid) (PLGA).

13. The method of claim 12, wherein the nanoparticle further comprises a poly(lactic-co-glycolic acid)/polyethylene glycol (PEG) block copolymer, optionally wherein the content of PEG relative to PLGA is from 1% to 15%.

14. The method of claim 11, wherein the nanoparticle has a mean diameter of from 100 nm to 400 nm.

15. A method for treating triple-negative breast cancer in a subject in need thereof, comprising administering to the subject a therapeutically effective amount of a peptide comprising the amino acid sequence of SEQ ID NO: 5.

16. A method for treating non-small cell lung cancer in a subject in need thereof, comprising administering to the subject a therapeutically effective amount of a peptide comprising the amino acid sequence of SEQ ID NO: 5.

* * * * *